US012620037B2

(12) United States Patent
George

(10) Patent No.: US 12,620,037 B2
(45) Date of Patent: May 5, 2026

(54) ON-BOARD SATELLITE CROPLAND ANALYSIS APPARATUS AND METHOD OF USE THEREOF

(71) Applicant: Thomas George, Los Angeles, CA (US)

(72) Inventor: Thomas George, Los Angeles, CA (US)

( * ) Notice: Subject to any disclaimer, the term of this patent is extended or adjusted under 35 U.S.C. 154(b) by 537 days.

(21) Appl. No.: 17/975,041

(22) Filed: Oct. 27, 2022

(65) Prior Publication Data

US 2024/0144395 A1 May 2, 2024

Related U.S. Application Data

(63) Continuation-in-part of application No. 17/974,975, filed on Oct. 27, 2022, which is a continuation-in-part (Continued)

(51) Int. Cl.
*G06Q 50/02* (2024.01)
*A01G 25/16* (2006.01)
(Continued)

(52) U.S. Cl.
CPC ........... *G06Q 50/02* (2013.01); *B64G 1/1021* (2013.01); *G01N 33/0098* (2013.01); *G01W 1/10* (2013.01);
(Continued)

(58) Field of Classification Search
CPC ...... G06V 20/188; G06V 20/13; G06Q 50/02; A01G 25/16; G06T 2207/10032;
(Continued)

(56) References Cited

U.S. PATENT DOCUMENTS

2014/0107957 A1* 4/2014 Lindores ................ G01D 18/00
702/85
2018/0077852 A1* 3/2018 George .................. A01G 25/16
(Continued)

OTHER PUBLICATIONS

Werle et al. (Spectroscopic gas analyzers based on indium-phosphide, antimonide and lead-salt diode-lasers, Spectrochimica Acta Part A: Molecular and Biomolecular Spectroscopy, vol. 58, Issue 11, 2002, pp. 2361-2372, ISSN 1386-1425, https://doi.org/10.1016/S1386-1425(02)00051-3.) (Year: 2002).*

(Continued)

*Primary Examiner* — Lisa M Caputo
*Assistant Examiner* — Christian T Bryant
(74) *Attorney, Agent, or Firm* — Kevin H. Hazen; Hazen Patent Group, LLC

(57) ABSTRACT

The invention comprises a method for managing cropland, comprising the steps of: (1) optically measuring level zero data with an orbiting satellite, the level zero data comprising: first reflected cropland radiation, in a visible range of 400 to 1,000 nm; second cropland radiation in a near-infrared range of 1,000 to 3,000 nm; third radiation in a range of 3,000 to 5,000 nm; and emitted radiation, in a thermal infrared range of 8,000 to 12,000 nm; (2) processing, on-board the orbiting satellite, the level zero data comprising a first data storage size, to yield cropland condition information comprising a second data storage size of less than one percent of the first data storage size; (3) receiving from the orbiting satellite to a ground-based communication system the cropland condition information; and (4) relaying at least a portion of the cropland condition information to a farmer within twenty-four hours.

20 Claims, 17 Drawing Sheets

Related U.S. Application Data of application No. 17/974,928, filed on Oct. 27, 2022, which is a continuation-in-part of application No. 17/974,879, filed on Oct. 27, 2022.

(51) Int. Cl.

| | |
|---|---|
| *B64G 1/10* | (2006.01) |
| *G01N 33/00* | (2006.01) |
| *G01W 1/02* | (2006.01) |
| *G01W 1/10* | (2006.01) |
| *G06V 20/13* | (2022.01) |
| *G06V 20/10* | (2022.01) |

(52) U.S. Cl.
CPC .............. *A01G 25/16* (2013.01); *G01W 1/02* (2013.01); *G01W 2203/00* (2013.01); *G06T 2207/10032* (2013.01); *G06T 2207/10044* (2013.01); *G06T 2207/10048* (2013.01); *G06T 2207/30188* (2013.01); *G06V 20/13* (2022.01); *G06V 20/188* (2022.01)

(58) Field of Classification Search
CPC . G06T 2207/10044; G06T 2207/10048; G06T 2207/30188; B64G 1/1021; G01N 33/0098; G01W 1/10; G01W 2203/00; G01W 1/02
See application file for complete search history.

(56) References Cited

U.S. PATENT DOCUMENTS

| | | | | |
|---|---|---|---|---|
| 2022/0256789 | A1* | 8/2022 | Heaven .............. | G01N 21/3554 |
| 2022/0270015 | A1* | 8/2022 | Vanderpool ............ | G06Q 50/02 |
| 2022/0390362 | A1* | 12/2022 | Liran ..................... | G06N 20/00 |

OTHER PUBLICATIONS

Dutch (Understanding data deduplication ratios, Data Management Forum, Jun. 2008) (Year: 2008).*
Kogan (Application of vegetation index and brightness temperature for drought detection, Advances in Space Research, vol. 15, Issue 11, 1995, pp. 91-100, ISSN 0273-1177, https://doi.org/10.1016/0273-1177(95)00079-T) (Year: 1995).*
Vaddi et al. ("A survey on Electromagnetic Radiation based Remote Sensing Applications to Agriculture," 2020 3rd International Conference on Intelligent Sustainable Systems (ICISS), Thoothukudi, India, 2020, pp. 1197-1202, doi: 10.1109/ICISS49785.2020.9316095) (Year: 2020).*

* cited by examiner

1700

ON-BOARD SATELLITE CROPLAND ANALYSIS APPARATUS AND METHOD OF USE THEREOF

CROSS REFERENCES TO RELATED APPLICATIONS

This application is a continuation-in-part of U.S. patent application Ser. No. 17/974,975 filed Oct. 27, 2022, which is a continuation-in-part of U.S. patent application Ser. No. 17/974,928 filed Oct. 27, 2022, which is a continuation-in-part of U.S. patent application Ser. No. 17/974,879 filed Oct. 27, 2022, all of which is incorporated herein in its entirety by this reference thereto.

BACKGROUND OF THE INVENTION

Field of the Invention

The invention relates generally to agriculture.

Discussion of the Prior Art

Patents related to the current invention are summarized here.

R. Lindores, et. al., "Wide-Area Agricultural Monitoring and Predicting", U.S. Pat. No. 8,731,836 (May 20, 2014) describe a ground based normalized difference vegetative index used to calibrate an aerial agricultural measurement.
Problem There exists in the art of agriculture a need for accurate, precise, and timely intervention to alter crop growing conditions.

SUMMARY OF THE INVENTION

The invention comprises an iteratively updated, multi-variate/multi-dimensional, and spatially resolved agriculture aid apparatus and method of use thereof.

DESCRIPTION OF THE FIGURES

A more complete understanding of the present invention is derived by referring to the detailed description and claims when considered in connection with the Figures, wherein like reference numbers refer to similar items throughout the Figures.

Elements and steps in the figures are illustrated for simplicity and clarity and have not necessarily been rendered according to any particular sequence. For example, steps that are performed concurrently or in different order are illustrated in the figures to help improve understanding of embodiments of the present invention.

DETAILED DESCRIPTION OF THE INVENTION

The invention comprises a method for managing cropland, comprising the steps of: (1) optically measuring level zero data with an orbiting satellite, the level zero data comprising: first reflected cropland radiation, in a visible range of 400 to 1,000 nm; second cropland radiation in a near-infrared range of 1,000 to 3,000 nm; third radiation in a range of 3,000 to 5,000 nm; and emitted radiation, in a thermal infrared range of 8,000 to 12,000 nm; (2) processing, on-board the orbiting satellite, the level zero data comprising a first data storage size, to yield cropland condition information comprising a second data storage size of less than one percent of the first data storage size; (3) receiving from the orbiting satellite to a ground-based communication system the cropland condition information; and (4) relaying at least a portion of the cropland condition information to a farmer within twenty-four hours.

Herein, the farmer is an example of a client or a consumer. More generally, the client is optionally any one or more of: a crop insurance company, an agriculture company, a farmer supply company, and/or a financial market/financial company.

Herein, a z-axis is aligned with gravity and an x/y-plane represents a place, such as cropland, perpendicular to the z-axis. As cropland is often not level, the cropland is optionally represented as a projection of the cropland along the z-axis onto the x/y-plane.

Herein, near-infrared light (NIR) light comprises light from 700 to 2500 nm and short wave near-infrared light comprises light from 700 to 1000 nm. Infrared light comprises: (1) short wave infrared light (SWIR) light from 700 to 1000 nm (2) NIR non-SWIR light from 1000 to 3000 nm; (2) mid-wave infrared (MIR or MWIR) from 3000 to 5000 nm (2000-3333 cm$^{-1}$ or wave numbers); and (3) long wave infrared (LWIR), also referred to as thermal infrared (TIR) from 8,000 to 12,000 nm (833-1250 cm$^{-1}$), which is the molecular "fingerprint region" to chemists.

Herein, spectral relates to and/or is made by a spectrum, especially relating to or derived from the electromagnetic spectrum of visible light and/or infrared light. Herein spectral data refers to one or more intensities of light detected at one or more wavelengths.

As further described, infra, a remote agriculture monitoring system yields simultaneous information on the state of growth, state of health, and/or future needs of spatially resolved sections of an agricultural area through use of remote spectroscopy, history, topography, and/or weather forecasts.

Figure 1:
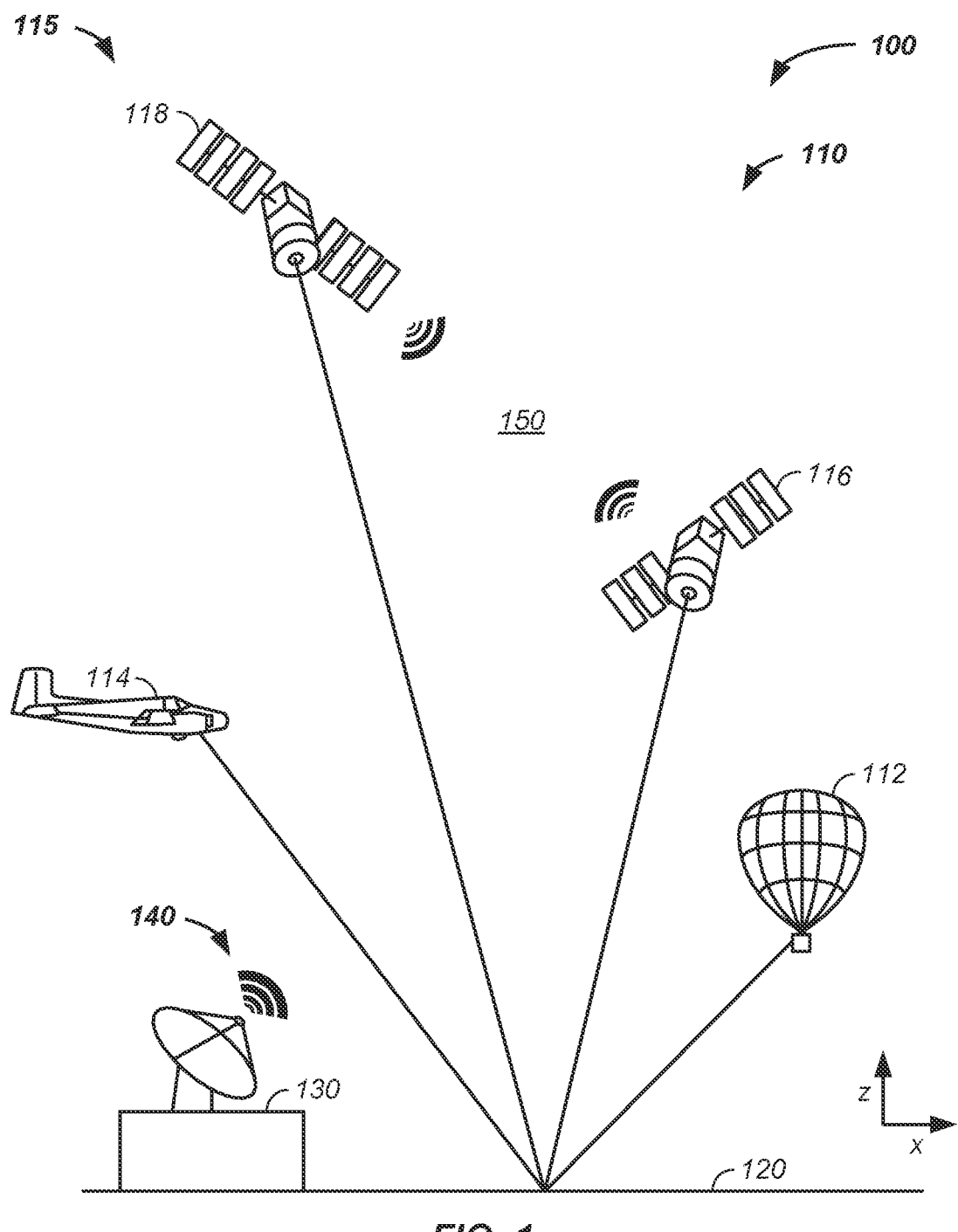
FIG. 1 illustrates remote monitoring of agricultural land.

Referring now to FIG. 1, a remote agricultural monitoring system 100 is described. For clarity of presentation and without loss of generality, the remote agricultural monitoring system 100 is described as a remote agriculture monitoring system. However, the time, space, and spectroscopy aspects as well as the data handling characteristics of the remote agriculture monitoring system also apply to climate, environmental monitoring, Department of Defense surveillance, mining, and/or any application of monitoring/measuring regions of the planet with emitted or reflected light.

Still referring to FIG. 1, as illustrated, one or more remote sensing platforms 110, of the remote agricultural monitoring system 100, are used to monitoring agricultural land 120, where at least a subset of gathered data is relayed, such as through wireless communication 140, to a base station 130 or a ground-based communication system. Optionally and preferably, the base station is on earth. As illustrated, the remote sensing platforms comprise one or more of: a balloon 112, an airplane 114, a satellite 115, such as a low earth orbit satellite 116, a high earth orbit satellite 118, and/or a geosynchronous satellite. However, any aerial and/or remote sensing platform is optionally used, such as a drone. As illustrated and as further described infra, the low earth orbit satellite 116 optionally communicates with the high earth orbit satellite 118 or vice-versa. In one case, as further described infra, compressed crop imaging data is sent from the low earth orbit satellite 116 to the high earth orbit satellite 118. Herein, for clarity of presentation and without loss of generality a satellite 115, such as the low earth orbit satellite 116 and/or the high earth orbit satellite 118, is used to refer to the remote sensing platform 110. Herein, a satellite 115 optionally refers to a group, cluster, and/or constellation of satellites. Any of the remote sensing platforms 110 carry one or more instruments for monitoring elevation, temperature, humidity, soil type, and/or spatially, temporally, and wavelength resolved light in the electromagnetic spectrum, such as in the visible, near-infrared, and infrared wavelength regions as further described infra. The remote sensing platform 110 optionally delivers the subset of the gathered data to a farmer and/or end user directly and/or indirectly such as via cell-phone, computer, and/or personal data assistant.

Figure 2:
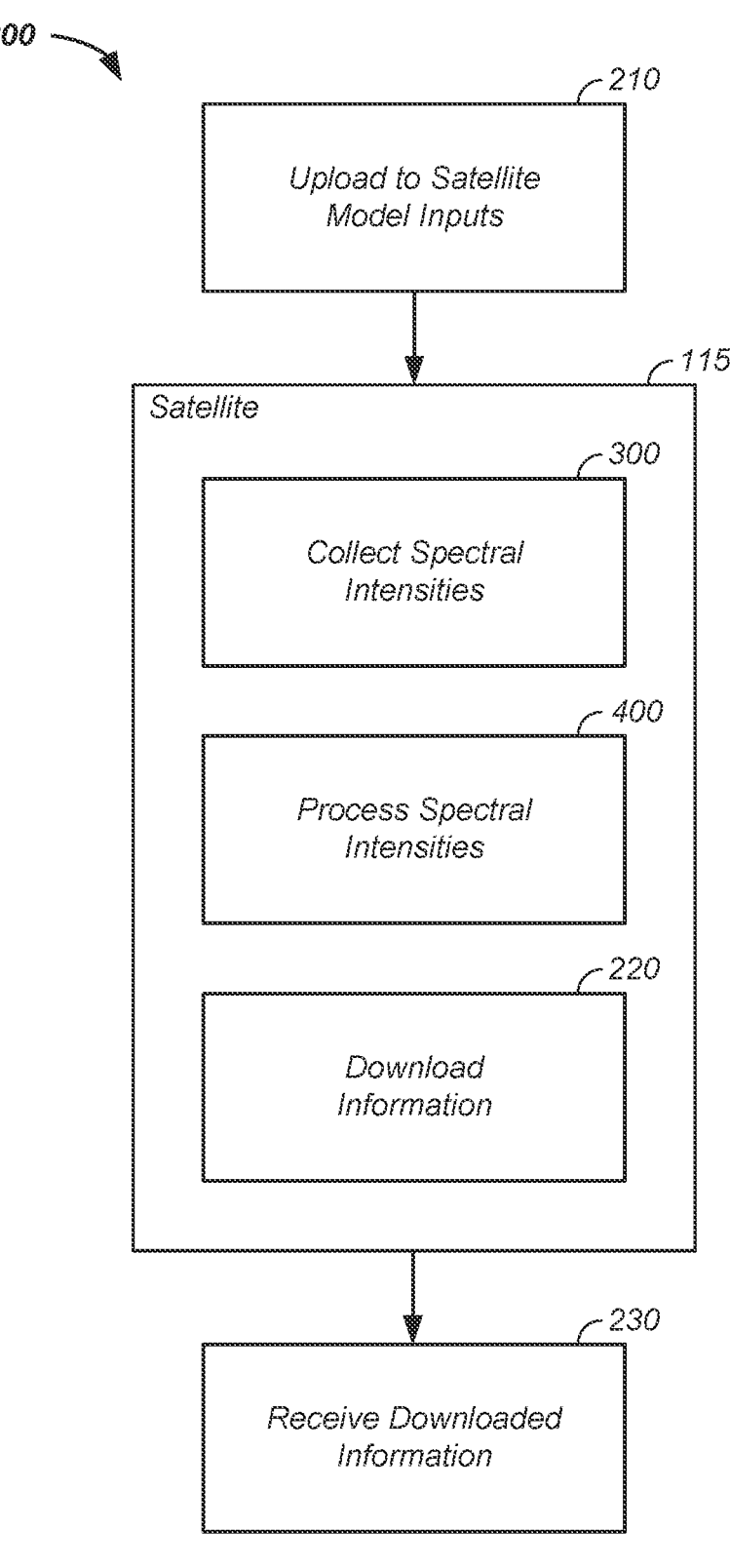
FIG. 2 illustrates on-board satellite processing of crop image data.

Referring now to FIG. 2, on-board satellite processing 200 is described. Optionally, one or more model inputs are uploaded 210 to the satellite 115, such as while the satellite 115 is in orbit. For instance, output of a weather model, crop information, and/or pest infestation information is provided to the satellite 115, such as for use in in a model. Generally, the satellite 115 collects spectral intensities, such as for any of the visible, short wave-infrared, non-shortwave infrared, and/or infrared regions described above. The satellite 115 further collects spatial information, such as with resolutions better than 1, 2, 5, 10, 20, 50, 100, 250, or 500 meters. As the satellite 115 moves relative to the earth, spatial resolution is also achieved around the planet. For instance, the satellite 115 may circle the earth about every 90 minutes. For one satellite, it takes about 17 days to return to the same position. To solve the latency problem, the satellite 115 is optionally a collection of satellites. A total of 15 satellites results in daily having a satellite in analysis range of a given plot of cropland. For instance, 14, 16, or 18±1 satellites are capable of repeating measurements at a particular location on earth daily. Herein, the satellites optionally and preferably wirelessly send information to each other in space 150, such as all or part of the raw data and/or all or part of a model input or output. For instance, the constellation of satellites are capable or spatially resolving a field of crops on a daily basis with any of the above defined resolutions, such as less than a 10 meter resolution, with one, two, three, or all of the wavelength regions described. As further described, infra, tighter wavelength resolution is optionally and preferably used, such as an ability to resolve differences in wavelengths of less than 1, 2, 5, 10, 20, 50, or 100 nm. As such, the amount of raw data collected is immense. Indeed, the amount of data is so large that it exceeds download capacities to the base station 130. Thus, optionally and preferably, the raw data is optionally and preferably processed 400 on-board the satellite 115. The processed output, such as from a model functioning on the satellite 115, optionally and preferably reduces that size of the raw data to a size of the processed data, where the processed data is less than 0.001, 0.01, 0.1, 1, 10, or 20 percent of a size of the raw data storage size and/or is reduced to a size of less than 100, 10, 1, 0.1, or 0.01 Mb or MB per hour. Optionally and preferably, downloaded information 220 includes the reduced size model output and/or a fraction thereof. Optionally and preferably, the downloaded information 220 does not include the raw data or more than 20% thereof. The downloaded information is received 230 on earth, such as by the base station 130. Optionally and preferably, the downloaded information 220, a part of the downloaded information, and/or information derived therewith is forwarded to a local consumer, such as a farmer within 1, 3, 6, 12, 24, 36, or 48 hours of collection of the raw data.

Still referring to FIG. 2, optionally one or more satellites of a constellation of satellites is configured to collect first spectral information, such as data over a first wavelength region. Similarly, optionally and preferably a different one or more satellites of the constellation of satellites is configured to collected second spectral information, such as data over a second wavelength region, where the second wavelength region does not overlap the first wavelength region. As above, raw data is optionally sent from one satellite to another satellite. However, the raw data size is optionally reduced in size, such as through use of a model and model results are optionally send from one satellite to another satellite, which again overcomes the bandwidth problems.

Figure 3:
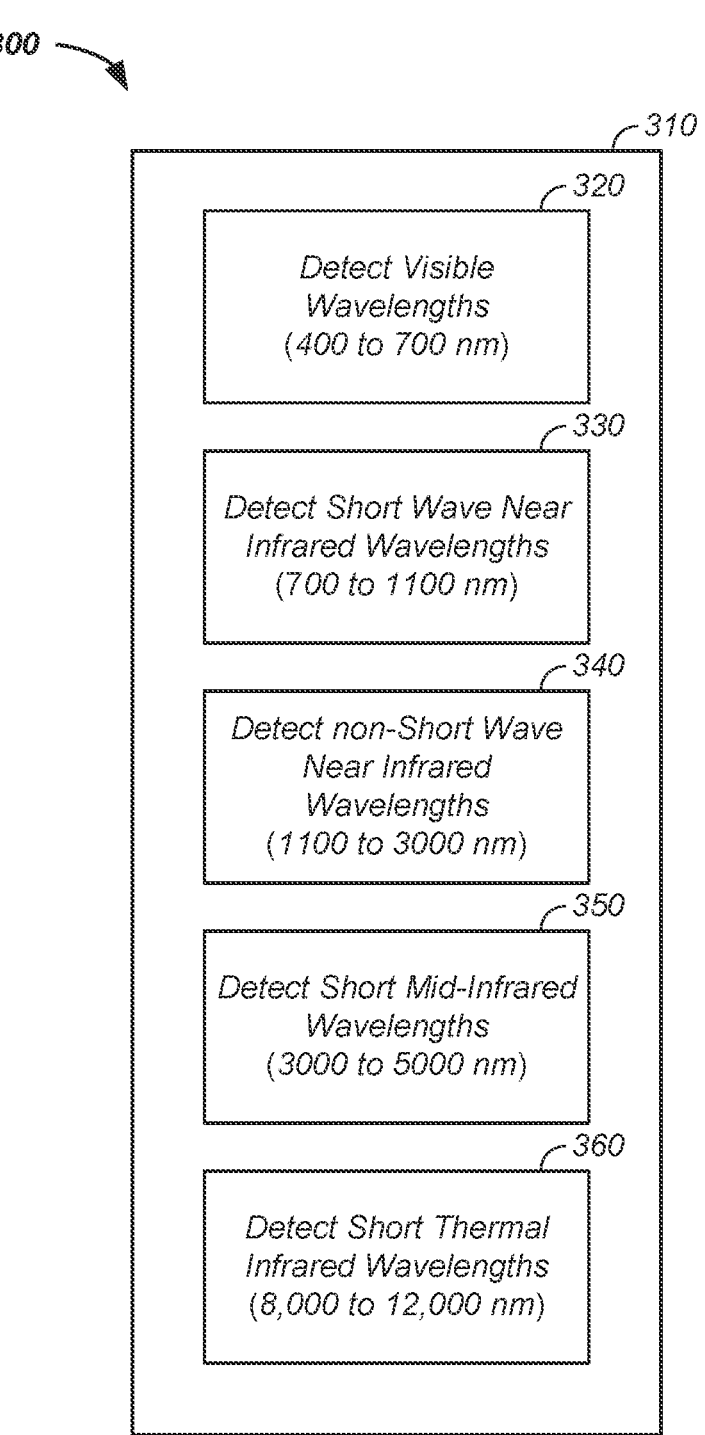
FIG. 3 illustrates analysis of cropland with various spectral regions.

Referring now to FIG. 3, wavelengths of collected/analyzed light 300 gathered by the satellite 115 are further described. Generally, the collected/analyzed light is measured in terms of intensity, current, and/or voltage, which is readily converted to another measure, such as transmittance and/or absorbance. The collected/analyzer light is optionally emitted light, such as heat energy, and/or is reflected light, such as reflected from the sun. One or more analyzers/spectrometers/spectrophotometers 310 are used to gather the spectral information, such as with any of the aforementioned wavelength resolutions. In a first example, a first analyzer 320 detects visible light, such as in a wavelength range of 400 to 700 nm. In a second example, a second analyzer 330 detects short-wave near-infrared light, such as in a range of 700 to 1000 nm. In a third example, a third analyzer 340 collects light in the traditional, non-short wave, near-infrared region, such as from 1000 to 2500 or 3000 nm. In a fourth example, a fourth analyzer 350 collects light in the mid-infrared region of 2500 or 3000 to 5000 to 8000 nm. In a fifth example, a fifth analyzer 360 collects light in the short thermal infrared wavelengths of 5000 or 8000 to 12,000 nm. Certainly, one analyzer is optionally configured to collect light in one or more of the aforementioned regions. For instance, a spectrometer configured with a silicon detector is optionally used to collect light in the visible and short-wave near-infrared regions. Similarly, an analyzer configured with a mercury cadmium telluride detector is optionally used to collect light in the non-short wave infrared and infrared spectral regions. Optionally and preferably, the each satellite 115 is configured with at least 1 and preferably 2, 3, 4, or more spectral analyzers.

Figure 4:
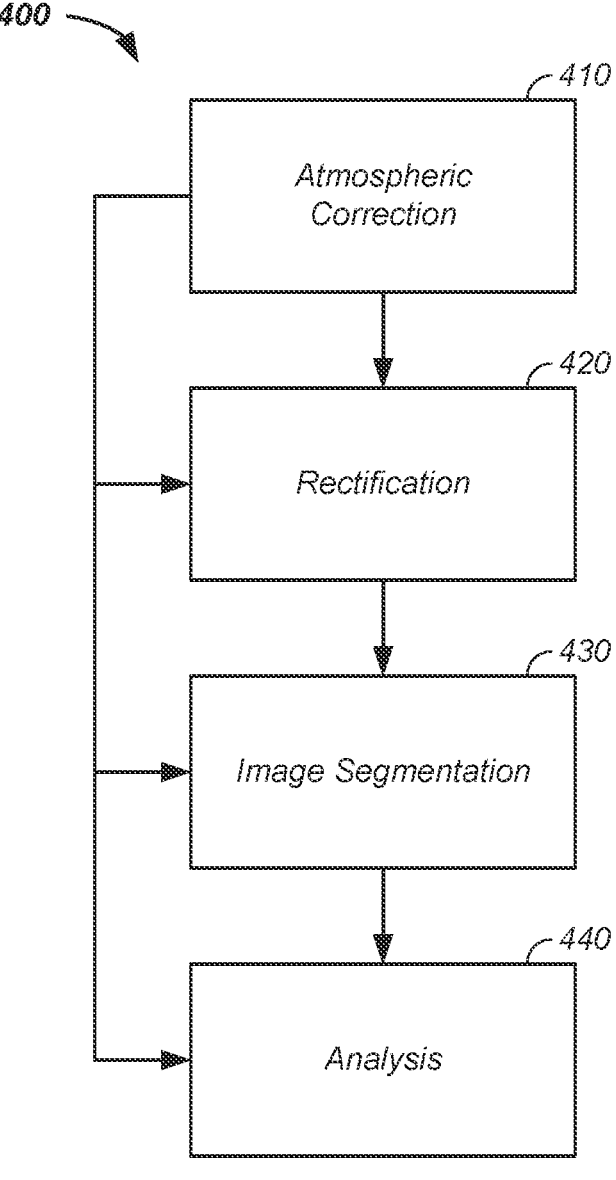
FIG. 4 illustrates image rectification.

Referring now to FIG. 4, on-board satellite processing steps 400 are further described. Typically, data from a satellite is processed on earth, which requires that the raw data is transmitted from the satellite to a station on earth for processing. However, as described supra, the large size of the raw data requires a lot of time to download to earth, which hinders timely use of the collected crop data. Ideally, crop information is relayed to a farmer within 24, 36, or 48 hours of collection, otherwise the information loses relevance for farm management. Thus, steps that have before now been performed on earth are optionally done on the satellite while in orbit. Again, the intent of the on-board satellite processing is to reduce the large raw data size to model output size for a fast download to earth for timely use. Hence, steps of instrument parameter correction, atmospheric correction 410, geo-rectification 420, image segmentation 430, and/or data analysis 440 are optionally and preferably performed on-board the satellite 115. Atmospheric correction 410 is an algorithmic correction of detected thermal radiance and/or detected reflected light to adjust for atmospheric conditions, such as cloud cover, water vapor content, and/or thermal impacts, such as on the light path and/or wavelength shift of an absorbance band, such as a water absorbance temperature dependency. Rectification 420 maps a satellite acquired two-dimensional image to a three-dimensional topography of the earth surface, such as hillsides, such as use of an elevation model combined with either a latitude and longitude or Mercator projection. Segmentation 430 classifies image elements into land cover components, such as cropland, roads, or buildings. As described, infra, the satellite 115 is optionally configured with uploaded spectral libraries used to identify crop type and/or crop developmental stage.

Still referring to FIG. 4, on-board satellite processing steps 400 have approximate and/or identical counterparts of land-based analyses, referred to herein as Level 0 to Level 4 data. The various data levels (0-4) are summarized in Table 1. NASA Level 0 to Level 4 and sublevel descriptions, optionally achieved on-board the satellite 115, are further described in Table 2.

TABLE 1

Data Level (Brief Description)

| Data Level | Description |
| --- | --- |
| Level 0 | Raw Data |
| Level 1 | Time referenced and annotated raw data |
| Level 2 | Derived geophysical variables at same resolution as Level 1 |
| Level 3 | Variables mapped on uniform space-time grid |
| Level 4 | Model output |

TABLE 2

Data Level (Description)

| Data Level | Description |
| --- | --- |
| Level 0 | Reconstructed, unprocessed instrument and payload data at full resolution, with any and all communications artifacts (e.g., synchronization frames, communications headers, duplicate data) removed. (In most cases, |

TABLE 2-continued

Data Level (Description)

| Data Level | Description |
| --- | --- |
| | NASA's EOS Data and Operations System [EDOS] provides these data to the DAACs as production data sets for processing by the Science Data Processing Segment [SDPS] or by one of the SIPS to produce higher-level products.) |
| Level 1A | Level 1A (L1A) data are reconstructed, unprocessed instrument data at full resolution, time-referenced, and annotated with ancillary information, including radiometric and geometric calibration coefficients and georeferencing parameters (e.g., platform ephemeris) computed and appended but not applied to L0 data. |
| Level 1B | L1B data are L1A data that have been processed to sensor units (not all instruments have L1B source data). |
| Level 1C | L1C data are L1B data that include new variables to describe the spectra. These variables allow the user to identify which L1C channels have been copied directly from the L1B and which have been synthesized from L1B and why. |
| Level 2 | Derived geophysical variables at the same resolution and location as L1 source data. |
| Level 2A | L2A data contains information derived from the geolocated sensor data, such as ground elevation, highest and lowest surface return elevations, energy quantile heights ("relative height" metrics), and other waveform-derived metrics describing the intercepted surface. |
| Level 2B | L2B data are L2A data that have been processed to sensor units (not all instruments will have a L2B equivalent). |
| Level 3 | Variables mapped on uniform space-time grid scales, usually with some completeness and consistency. |
| Level 3A | L3A data are generally periodic summaries (weekly, ten-day, monthly) of L2 products. |
| Level 4 | Model output or results from analyses of lower-level data (e.g., variables derived from multiple measurements). |

Still referring to FIG. 4, segmentation 430 is further described. Typically, segmentation 430, which is classification of land cover elements, of the satellite images is done on earth. However, as described supra, segmentation 430 is optionally and preferably performed on the satellite 115. Optionally, segmentation 430 includes an additional step of crop type determination and/or crop developmental stage determination. To aid the segmentation step 430, one or more spectra, such as in the form of a spectral library, are optionally and preferably uploaded to the satellite 115 prior to launch and/or while in orbit. Stated again, a spectral library is optionally used in segmentation 430 to identify a particular crop type in a particular area by comparing known spectral features with measured spectral features.

Still referring to FIG. 4, data analysis 440 is further described. Generally, data analysis 440 is used to determine a state of spatially resolved crop land, such as a crop temperature, a need to water, a fertilizer recommendation, and/or a disease/fungal/weed/pest control step. The data analysis 440 is further described, infra.

Figure 5:
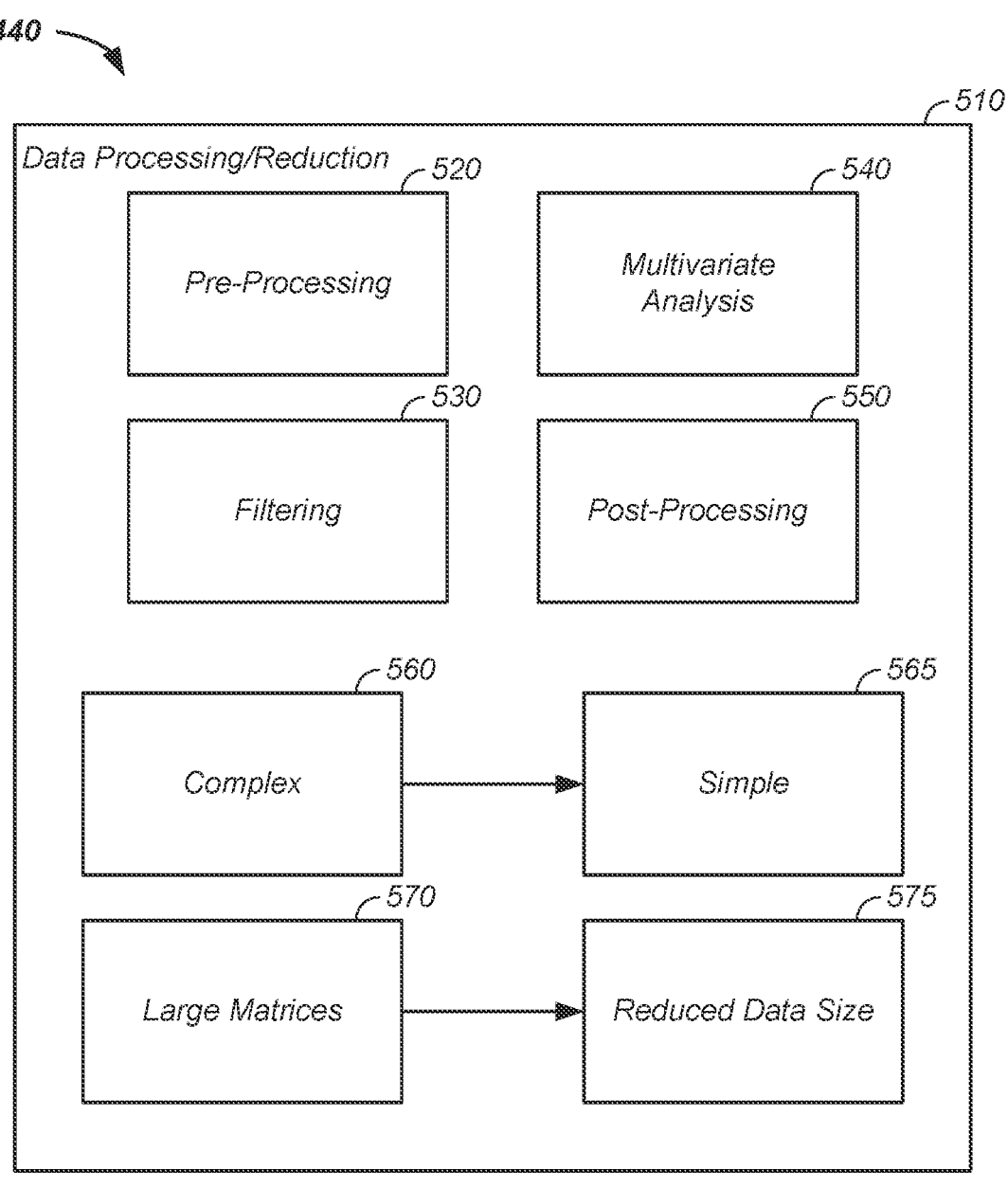
FIG. 5 illustrates data processing and data reduction.

Referring now to FIG. 5, data analysis 440 is further described. Generally, data analysis 440 includes a data processing/data reduction step 510. For example, the data processing/reduction step 510 optionally includes a pre-processing step 520, a filtering step 530, a multivariate analysis step 540, and/or a post-processing step 550. Main goals are to move from complex data 560, such as large/raw data matrices to simple outputs 565, such as information derived from data. That said, complexity in the raw data i.e., high resolution along the spatial, temporal and spectral information axes, is desired in the raw data in order to minimize error in the form of false positives or false negatives in the output, derived information. Examples of "simple" output information include, for a spatially resolved piece of cropland: a determined temperature and the corresponding health or stress state of the crops, and farm management prescriptions for targeted irrigation, fertilizer, antibiotic, fungicide, pesticide and herbicide applications, as needed, and only in areas requiring such treatment, a determined developmental stage of the crops, an expected developmental stage of the crops. Stated again, the data processing/reduction step 510 analyzes large, high-complexity matrices 570 and creates reduced data size 575 actionable information outcomes, such as the aforementioned crop properties and targeted crop prescriptions. Data analysis 440 is further described infra in a series of non-limiting examples.

Spatial Resolution

In this section, spatial resolution is addressed. However, the spatial resolution aspects described herein function in conjunction with wavelength resolution and temporal analysis, each of which are further described supra and infra.

Figure 6:
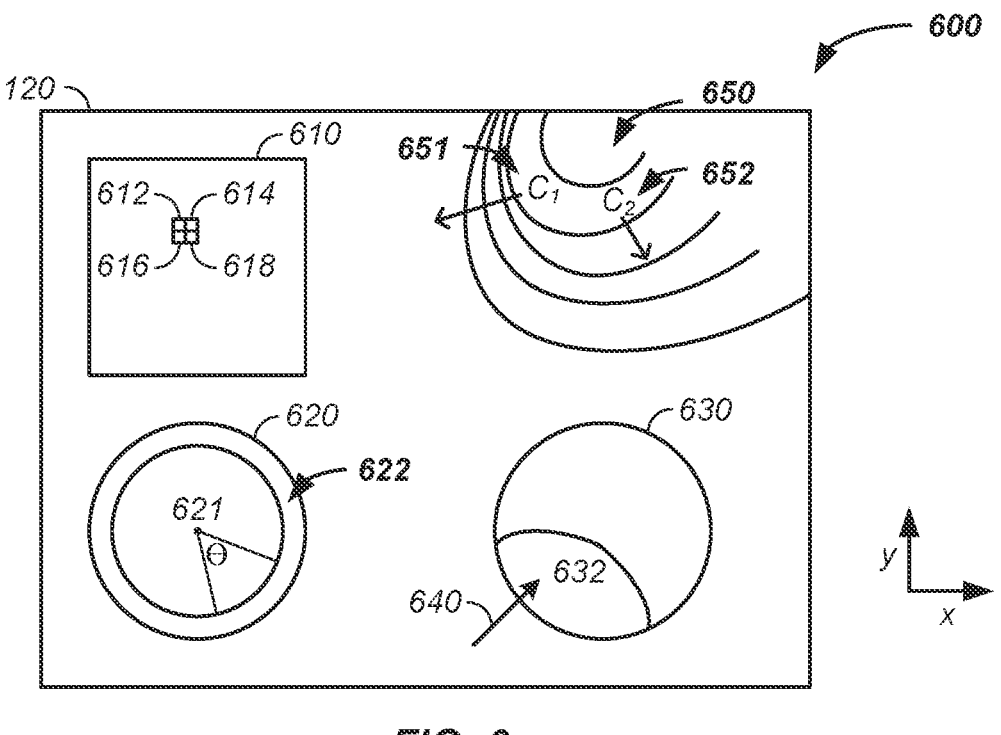
FIG. 6 illustrates spatially resolved monitoring of agricultural land.

Referring now to FIG. 6, a spatially resolved monitoring system 600 is described for monitoring the agricultural land 120. For clarity of presentation and without loss of generality, several spatial monitoring examples are provided.

Example I

Still referring to FIG. 6, a first example of use of the spatially resolved monitoring system 600 is described. In this example, an agricultural field 610 is monitored. As illustrated, the agricultural field is made up of an array of spatial sub-elements. Here, a first spatial sub-element 612, a second spatial sub-element 614, a third spatial sub-element 616, and a fourth spatial element 618 of n spatial elements of the field are monitored, where n is a positive integer. Optionally and preferably, spatial resolution of the remote agricultural monitoring system is less than 1, 5, 10, 20, 25, or 50 meters. Typically, a 10 meter spatial sub-element is sufficient to make enhanced agricultural decisions. Detector element sizes and coupling optics on the one or more detector arrays on the satellite 115 are optionally and preferably configured to match the desired ground spatial resolution in each wavelength range used.

Example II

Still referring to FIG. 6, a first central pivot crop circle 620 is illustrated. While the farmer may guess that the crops in general need water through visual inspection and/or may guess that the crops need more fertilizer through experience, remote spectroscopy generates a quantitative metric of specifically how much additional irrigation/water and/or fertilizer and/or crop protection is necessary and at which geo-locations, the so-called variable rate agriculture. Further, remote spectroscopy optionally and preferably yields information on thee application requirements for individual spatially resolved areas of each cropland area and does so without a required visual inspection by the farmer. In this example, the remote agricultural monitoring system 100 combines reflected and/or emitted light intensities as a function of wavelength, as further described infra, with a historical context of irrigation/fertilizer/crop protection application to remotely yield actionable information, and in the specific case of pivot irrigation, for the entire area of the first central pivot crop circle 620 requiring a fertilizer and an outer perimeter area 622 requiring extra watering. Key here is that the spatial resolution, described in the previous example, is combined with remote spectroscopy and optionally with historical information to yield actionable information on targeted fertilizing, crop protection, and/or watering particular areas of the crop in the first pivot crop circle. Particularly, a fertilizer may be added to the watering system, the so-called fertigation, for a first watering period and the pivoting irrigation system could be configured with extra pressure to apply the water and fertilizer to the outer perimeter area 622. In this example, the inner region of pivot crop circle was identified as not needing the fertilizer, so a lower pressure is applied to water the central area and fertilizer is not applied in a second watering period.

Example III

Still referring to FIG. 6, a third example of spatial resolution is described. In this example, the first central pivot crop circle 620 is illustrated with a region from a central point 621 expanding outward at an angle theta, e, that is identified by the remote spectroscopy as requiring additional water and/or fertilizer. When watering the identified sector, additional water and/or added fertilizer is applied to the identified stressed crop region.

Example IV

Still referring to FIG. 6, a second central pivot crop circle 630 is illustrated. In the second pivot crop circle 630 a treatment area 632 is identified, such as the southwest region of the second pivot crop area. The treatment area 632 indicates that the crops are stressed in some manner, such as a pest infestation, need of fertilizer, and/or water requirement. Here, the remote agricultural monitoring system 100 combines reflected light intensities as a function of wavelength, as further described infra, with a weather forecast report of a southwest wind and dry conditions to remotely yield actionable information of having the rotating irrigation system, of the second central pivot crop circle 630, deliver extra water from about the 5 o'clock to 8 o'clock position.

As further described, infra, weather models, pest information, and/or other model parameter inputs are optionally uploaded to the satellite 115. The satellite 115 includes a main controller that processes imagery, such as intensities of observed light as a function of wavelength, time, and/or position. As part of the processing step, the uploaded inputs are optionally used, such as in a model. Model outputs, representing vastly compressed data in the form of extracted information is then sent back to the base station 130 in a timely manner as the information requires less bandwidth to send back than the typically gigabytes of raw collected spectral data.

Example V

In a fifth example, not illustrated, a third central pivot crop circle, as analyzed by the remote agricultural monitoring system 100, requires all of the treatments of the previous two examples: a fertilizer over the entire crop, extra irrigation over an outer perimeter area, and extra irrigation over a southwest region.

Example VI

Referring again to FIG. 6, in a sixth example the remote agricultural monitoring system 100 combines absorbance/diffuse reflectance/emittance spectra with topography information to generate a recommended treatment of spatially resolved sections of the agricultural land 120. Herein, the remote sensing platform 110 optionally determines topography 650 of the spatially resolved sections of the agricultural land 120 and sections abutting against and/or within less than 20, 30, 40, or 50 meters or uses a topography database to alter a non-topography modified recommendation. For example, at a first point 651 a steep contour is observed on a topography graph and at a second point 652 a smoother contour area is observed. A main controller of the base station 130 and/or the satellite 115 optionally adjusts the applied and/or recommended concentration of fertilizer upward to compensate for an expected dilution of the fertilizer with water facilitated transport down the hill and conversely optionally adjusts a down the hill concentration of fertilizer to be applied downward in expectation of runoff of fertilizer from the uphill position.

Example VII

In a seventh example, a combination of signals are indicative of a stressed crop. For instance, as the water absorbance decreases, such as measured by the near-infrared water absorbance, described infra, the water present decreases, which at sufficiently low water absorbances is indicative of drought. Similarly, a thermal shift of black body temperature to shorter wavelengths, such as in the 8,000 to 12,000 nm region, is indicative of warmer soil and/or decreased vegetative cover, which is also indicative of drought. On-board the satellite both processes are observed and are optionally fused in a drought analysis, such as via comparison with a spectral library of drought states. The same indicators are optionally indicators of pests, such as observed from 1,000 to 2,500 nm, and/or disease, such as observed from 1,000 to 2,500 nm. Again, the on-board spectral library is used as a comparator, where the spectral library has examples of various stages of drought, pest infestation, and/or disease.

Example VIII

In an eighth example, a stressed crop may show decreased or even essentially stopped transpiration, which is observed by looking at the water bands, such as described herein.

Example IX

In a ninth example, effects of applied fertilizer and/or a need for fertilizer is measured. Fertilizer yields more green in the crop growth. A decrease in green is an increase in absorbance of red light. Thus, the normalized difference vegetative index (NDVI), described supra, is a measure of fertilizer need.

More generally, the remote agricultural monitoring system 100 allows for monitoring tens, hundreds, and/or thousands of crop areas, such as central pivot crop circles and/or any geometrically shaped field, yields a quantitative metric for each sub-region, such as an individual central pivot crop circle; and/or yields a set of quantitative metrics, such as need for crop protection, herbicide, pesticide, fertilizer, tilling, crop rotation, and/or irrigation for each spatially resolved sub-element of each sub-region all without requiring a visual inspection by the farmer or any sub-region, much less all sub-elements, of the farm.

The inventor notes that output of the remote agricultural monitoring system 100 is optionally used in an automated control of one or more treatment/management systems of the farm sub-elements.

On-Board Processing

Figure 7:
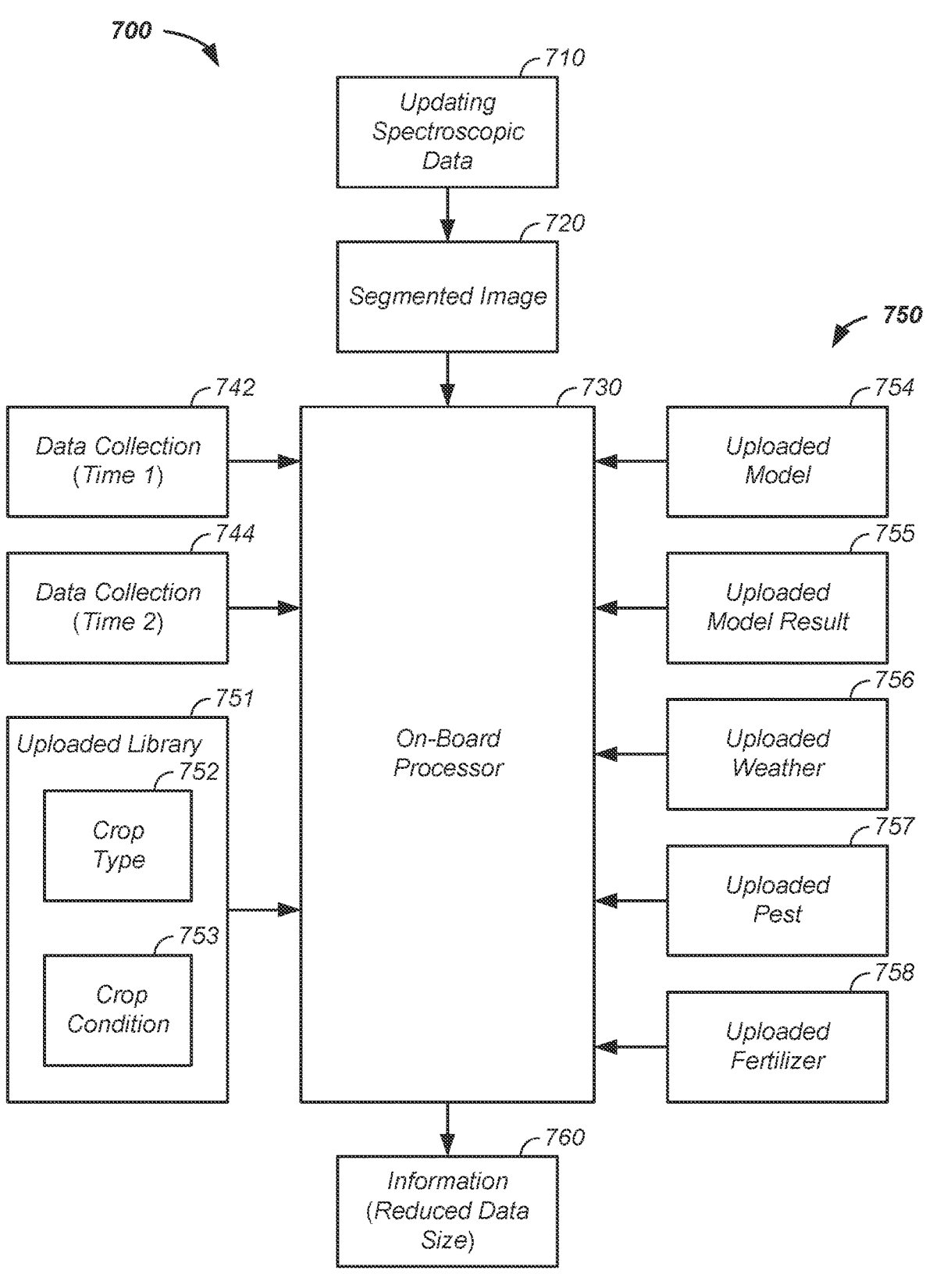
FIG. 7 illustrates on-board cropland image processing.

Referring now to FIG. 7, on-board processing 700, on the satellite 115 in orbit, is further described. Generally, the satellite 115 is used to update/collect new spectroscopic data 710, as described supra. The resulting collected raw data is processed. Here, a segmented image 720 is optionally additionally corrected with the atmospheric correction 410 and/or has undergone rectification 420, as described supra, such as with an on-board processor 730. The on-board processor 730 yields information 760 and/or a reduced size data set, as described supra. Inputs to the on-board processor are further described, infra.

Still referring to FIG. 7, the updated spectroscopic data 710 step is optionally repeated and stored n times, where n is a positive integer greater than 0, 1, 2, or 3. For instance, data collection occurs at a first time 742 resulting in a first data set. The first data set is analyzed to determine a first determined crop state, as typically for a spatially resolved region. An uploaded model 754, an uploaded model result 755, and/or an on-board model result, of a set of models 750, may indicate for the first determined crop state an expected crop state condition at a second (future) time. At the second time, a second data collection 744 occurs resulting in a second data set. Through comparison of a second determined crop state, for the spatially resolved region, a difference between: (1) the modeled/expected outcome and (2) the second crop state yields crop information, leading to a suggestion of watering, fertilizing, and/or pest control, as further described infra.

Still referring to FIG. 7, optionally, the satellite 115 includes one or more uploaded spectral libraries 751. An example of a first library is a crop type library 752. The crop type library contains spectral responses/spectral signatures for one or more crop types, such as corn, wheat, soybeans, or barley, which are examples of any crop type. Generally, the spectral responses/spectral signatures are used to remotely identify and distinguish crop types. The spectral responses/spectral signatures are for any wavelength range and/or any operational mode of any spectrometer(s) carried by the satellite. An example of a second library is a crop condition library 753. The crop condition library 753 contains spectral characteristics of a given crop as a function of time, stress, and/or condition. For example, the crop condition library contains, for one or more crop types, expected spectral characteristics of the crop, such as at 1, 2, 3, 4, . . . , 98, 99, 100 days past planting and/or past sprouting. For instance, at 10 days past sprouting, a lot of dirt/earth is expected in the image and a smaller percentage of green is expected. Naturally, the expected percent green increases with time post planting as the crops grow. This library is thus used as a comparison against the measured crop, as part of a crop health determination. Too little green might indicate lack of water and/or lack of fertilizer. In a second example, the crop condition library 753 optionally contains spectra/spectral characteristics of a crop with too little or too much fertilizer as a function of time since planting. In a third example, the crop condition library 753 optionally contains spectral information on too little and/or too much water as a function of time, as is further discussed infra. In a fourth example, the crop condition library 753 optionally contains spectral information on affects of pest infestation, such as protein absorbance bands, crop color, crop cover percentage, and/or expected crop conditions as a function of time and/or as a function of pest infestation type/pest infestation rate.

Still referring to FIG. 7, one or more models and/or model results 750 are optionally uploaded to the satellite 115 while the satellite is in orbit. For example a model is uploaded 754 and/or a model result 755 is uploaded to the satellite 115 while the satellite 115 is in orbit. For instance, weather, a weather model, and/or a weather prediction 756 is optionally uploaded to the satellite. Thus, the on-board processor 730 on the satellite 115 may incorporate weather in the orbiting on-board data processing of the gathered spectroscopic data 710. For instance, a measurement of current crop moisture is combined with expected precipitation on-board the satellite 115 so that the reduced size data matrix downloaded and distributed to the farmer includes a more accurate prediction of crop watering needs. Similarly, pest information 757 is optionally uploaded to the satellite 115, which is used in the on-board processing. For instance, a trend of pest infestation spreading toward an analyzed area is used to predict pest infestation of the analyzed area, where the on-board processing is optionally and preferably enhanced using weather, water, crop type, and/or crop state information. Similarly, information from the farmer, such as applied fertilizer 758, is uploaded to the satellite 115, such as via the base station 130. Thus, the on-board processor 730 optionally and preferably combines the fertilizer application to the raw and/or on-board processed data to yield better predictions for the farmer to follow. Several examples of on-board processing with the on-board processor 730 follow where time, space, and spectral information are distilled, on-board the satellite 115, into actionable information.

Wavelength Resolution

In this section, remote spectroscopy measurements as a function of wavelength and/or in sections of the electromagnetic spectrum are described. However, the remote spectroscopy functions together with the spatial resolution, described supra, and the temporal analysis, described infra.

Figure 8:
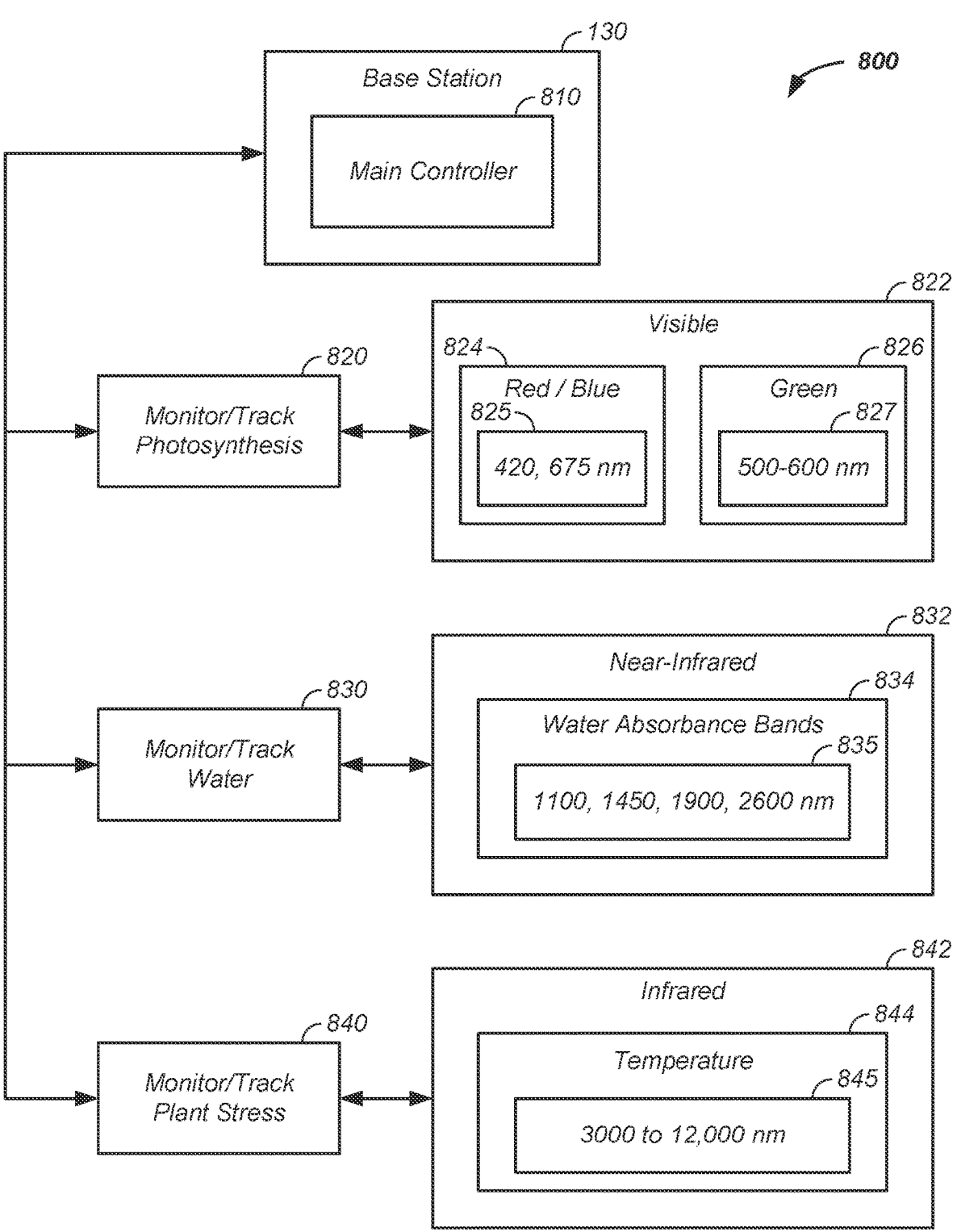
FIG. 8 illustrates monitoring agricultural land using multiple regions of the electromagnetic spectrum.

Referring now to FIG. 8, remote spectroscopy 800 cropland analysis is described using the visible, near-infrared, and infrared regions of the electromagnetic spectrum. For clarity of presentation and without loss of generality, particular wavelengths are used. However, it is recognized that a mean width of an absorbance is wavelength dependent and generally increases with decreasing wavelength. As illustrated, the base station 130 contains the main controller 810, such as housing the on-board processor 730. The main controller 810 is directly and/or indirectly linked to the remote sensing platform 110, any intermediate analysis device, any intermediate user, and/or the final user. Generally, cropland analysis uses a combination of three regions of the electromagnetic spectrum: the visible region, the near-infrared region, and the mid-infrared region. Though described separately, the inventor notes that the synergy of combining related information from the multiple wavelength regions is greater than a sum of analyses of the individual wavelength regions.

As described supra, the remote sensing platform 110, satellite 115, spatially resolves the agricultural land 120. More particularly, the remote sensing platform 110 uses one or more two-dimensional detector arrays coupled to an optical imaging system to spatially resolve sections of the agricultural land 120. Further, for each spatially resolved section, of the agricultural land 120, responses are independently measured at multiple wavelengths, such as two or more wavelengths in the visible region and two or more wavelengths in the near-infrared region, and two or more wavelengths in the mid-infrared region. Wavelengths of light are separated, resolved, and/or isolated using a set of optical filters, a grating based spectrometer, a movable mirror based spectrometer with a subsequent Fourier transform, a Hadamard based analyzer, and/or a wavelength separation device. Optionally and preferably, two or three spectrometers, analyzers, wavelength separation approaches, and/or two-dimensional detectors are used to cover the range of wavelengths of interest from about 380 nm to about 12,000 nm, where detectors include silicon based, indium gallium arsenide based, and/or mercury/cadmium/telluride based detector elements. Resulting signals are optionally and preferably fused, such as after a spatial resolution transform into a resulting data cube. The data cube comprises two axes comprising a projection of the agricultural land 120 along the z-axis onto and x/y-plane of the detector and for each m×n detector element a spectrum, S, is recorded, where the spectrum, S, represents signals from the one, two, three, or more spectrometers. Subsequent data cubes are generated as a function of time, as further described infra. The large data cubes are optionally subsequently analyzed using hardware on the satellite 115 and a smaller resulting data/information set is transmitted back to the main controller 810 of the base station 130 and/or is transmitted to the end user or equipment thereof directly, as described infra. A data cube is optionally broken or separated into component parts, matrices, indices, and the like where the combined data of the individual parts is a subset of the original data cube, a transformation of the original data cube, or a representation of the data cube where underlying information of the combined separated parts includes x/y-position information and remote sensing spectroscopy information associated with the x/y-positions. A processed data cube is referred to herein as an information cube. The information cube comprises a transform of the data cube into an n-dimensional space where the n-dimensional space comprises fewer dimensions than individual wavelength regions measured and placed into the data cube. Optionally and preferably, the information cube is supplemented with additional information, such as by fusion, concatenation, and/or a further transform with non-spectral information, such as further described infra.

The data cube is optionally supplemented with non-spectral data/information, such as: underground features; water holding capacity of the soil; soil type, such as clay or sand; tilth; soil depth; rock features; heat holding capacity; and/or localized heat holding features, such as roadways, rock walls, and water bodies, where the non-spectral data/information is optionally preinstalled on the satellite 115 and/or is uploaded to the satellite 115 in orbit.

Example I

Referring still to FIG. 8, a first example of remote spectroscopy 800 is described using visible light 822 from 400 to 700 nm and/or within 50 nm of the visible light to monitor/track an agricultural parameter. For clarity of presentation and without loss of generality, photosynthesis 820 is used as a process monitored in the visible region 822. More particularly, chlorophyll absorbance and reflectance is used to further describe the remote agricultural monitoring system 100. However, the chlorophyll absorbance and reflectance description is representative of remote sensing of other processes/process results, such as: (1) oxygen release during photosynthesis, with oxygen absorbance bands at 755 to 775 nm and 689 to 695 nm, optionally analyzed with polarization techniques and (2) evapotranspiration yielding temperature reduction and water, where the water bands are further described infra.

Optionally and preferably, sunlight is used as a source of visible photons. Red and blue 824 wavelengths of sunlight are absorbed by chlorophyll while the green 826 of green crops represents reflected green light.

More particularly, chlorophyll comprises chlorophyll a and chlorophyll b. Generally, chlorophyll a comprises peak absorbances 325 at 420±10 nm and 675±10 nm and chlorophyll b comprises peak absorbances at 470±15 nm and 625±20 nm. However, chlorophyll absorbs broadly in both the blue and red regions of the electromagnetic spectrum. Hence, absorbance is optionally measured at and/or within ±30, 50, 75, or 100 nm from the peak absorbance.

Still more particularly, as chlorophyll absorbs red and blue light, reflected light is optionally used to measure chlorophyll, where chlorophyll is used as an indirect indicator of crop health. For instance, reflected and/or diffusely reflected: (1) green light 327, such as from 500 to 600; (2) ultraviolet light, such as from 200 to 400 nm; and/or (3) near-infrared light, such as from 700 to 1000 nm is used to determine a first health parameter of the crops, being related to the green vigor of the plant and the chlorophyll therein. The inventor notes that non-green light from 480 to 500 nm and/or 600 to 620 nm is optionally used to measure crop health as chlorophyll absorbance drops to less than five percent above 480 nm and rises above five percent at 620 nm.

Optionally and preferably, intensities of multiple visible wavelengths are detected allowing non-linear data analysis and/or chemometric analysis to extract more detailed, accurate, and/or precise sample constituent information. Optional data analysis techniques include: hyperspectral imaging using combinations of wavelengths from the visible, near-infrared, and infrared wavelength regions; multivariate approaches, such as use of partial least squares or principal component regression; artificial intelligence, such as a neural network; a calibration data set used to generate a model for subsequent prediction of values from subsequent measurements; multi-modal measurements, such as temperature, wind speed, humidity, topography, precipitation, time of day, and wavelength intensity information; and/or combining intelligent system information, such as historical information with any of the preceding techniques.

Generally, reflected/diffusely reflected visible light allows the sun to function as the source and to use an intensity detector positioned above the crops, such as carried by the satellite 115, as described supra.

Example II

Still referring to FIG. 8 a second example of remote spectroscopy 800 is described using near-infrared light 832 from 700 to 2500 nm. For clarity of presentation and without loss of generality, monitoring water 830 and optionally tracking water concentration is used as an exemplary process monitored using the near-infrared region 832. Optionally and preferably, sunlight is used as a source of near-infrared. Water is optionally observed anywhere in the near-infrared region; however, preferred wavelengths are at water absorbance bands 834, such as peak water absorbances at 1100, 1450, 1900, and 2600 nm 835. More particularly, larger water absorbance at longer wavelengths results in a small mean depth of penetration of detected diffusely reflected sunlight at longer wavelengths. Thus, water content is measured in the outer quarter millimeter of a leaf of a crop from 2350 to 2600 nm and in the outer half millimeter from 2100 to 2350 nm. Greater mean depths of penetration of diffusely reflected light from a crop leaf is observed at shorter wavelengths, such as greater than one-half millimeter from 1500 to 1750 nm and greater than one millimeter from 1100 to 1350 nm or 700 to 1350 nm. Thus, a measure of crop hydration using the near-infrared region 332 is obtained using remote spectroscopy 800, such as from the satellite 115. Further, hydration of the leaves of the measured crop as a function of depth of penetration into the leaf is optionally measured using remote spectroscopy 800, which is a measure/quantitative measure of crop health.

Example III

Still referring to FIG. 8 a third example of remote spectroscopy 800 is described using infrared light 842. For clarity of presentation and without loss of generality, plant stress 840 and optionally tracking plant stress is performed through monitoring temperature 844 and optionally tracking temperature, such as through temperature determination using infrared light from 2500 to 12,000 nm 845 in the infrared region 842. Optionally, infrared light and/or changes in infrared light as a function of time is detected in twilight, dark, or dawn through detection photons radiating from stored heat sources to determine crop health and/or supplement the data cubes, described supra. Particularly, time-offset heat information is coupled to daytime data cubes through ground location indices.

Optionally and preferably, the crop and/or soil emits infrared light and the light is monitored directly, such as via an intensity versus position measurement, optionally at 1, 2, 3, 5, 10, 25, 50, 100 or more infrared wavelengths.

Example IV

Figure 9:
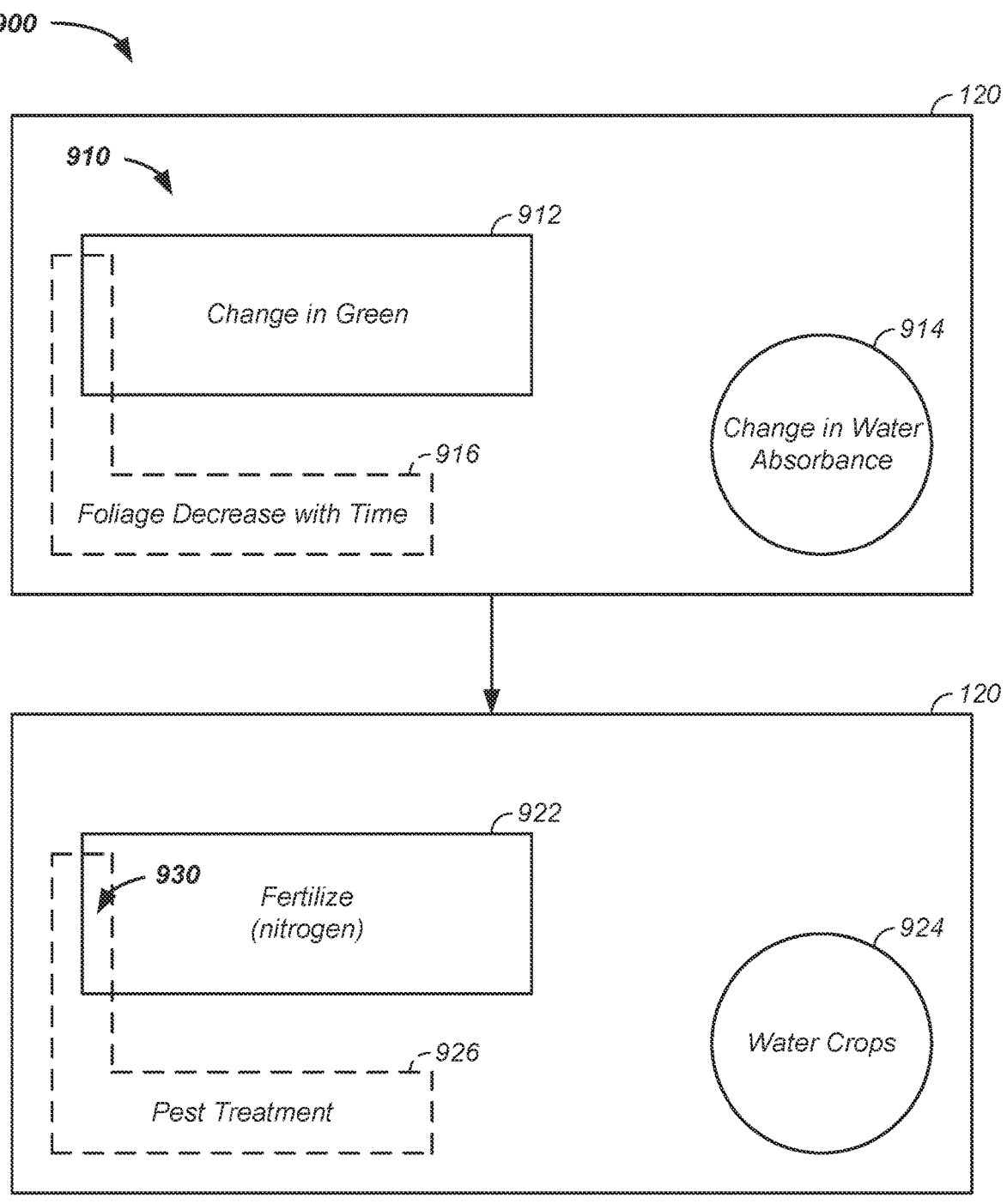
FIG. 9 illustrates combining multiple regions of spatially resolved light and resulting actionable intelligence.

Referring now to FIG. 9, monitoring crops using multiple regions of light 900, including at least two of and preferably all of the visible 822, the near-infrared 832, and the infrared 842 regions, is further described. In this non-limiting example, a set of crop areas 910 of the agricultural land 120 are simultaneously monitored as the satellite 115 moves over/by/past the agricultural land 120. More particularly: (1) a first crop area 912 reveals a decrease in diffusely reflected green light in the visible region; (2) a second crop area 914 reveals a change in water absorbance 914 in the near-infrared coupled with a more rapid temperature rise as a function of time of day, normalized by weather parameters, as observed in the infrared; and (3) a third crop area 916 reveals a foliage decrease through reduction in green in the visible region, a change in observed water absorbance in the near-infrared region, and more rapid temperature swings in the infrared region. Resulting actionable results/recommendations are to fertilize 922, water 924, and add pesticide 926 to the first, second, and third crop areas 912, 914, 916, respectively. Notably, an overlapping area 930 optionally receives more than one treatment type. Generally, the first, second, and third crop areas 912, 914, 916 respectively illustrate an analysis with one, two, and three of the visible, near-infrared, and infrared wavelength regions.

Temporal Analysis

In this section, temporal analysis of data from the above described spatial resolution and wavelength resolution is described.

Figure 10:
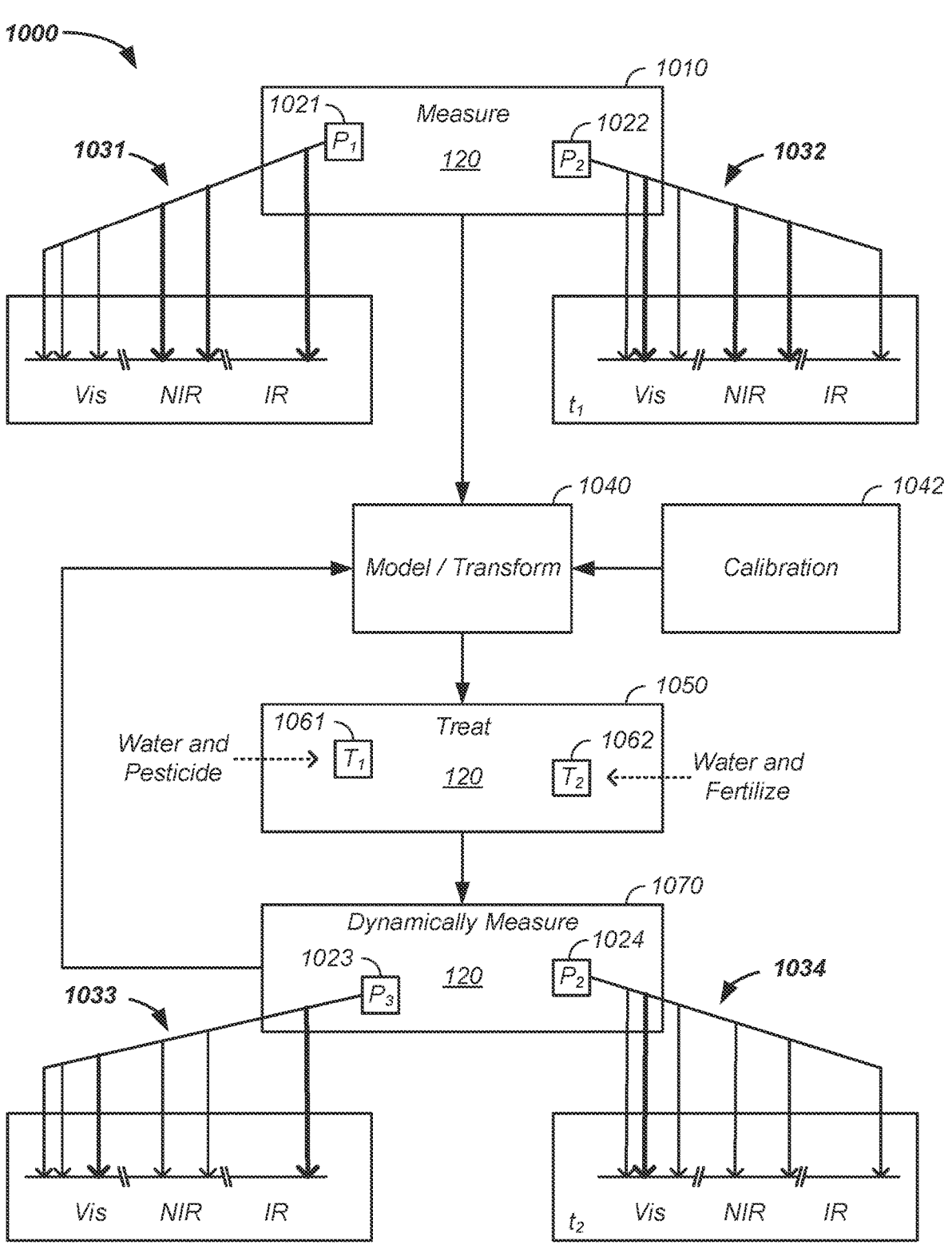
FIG. 10 illustrates agricultural monitoring using a dynamically updated, spatially resolved, and multi-region wavelength resolved system.

Referring now to FIG. 10, an iterative crop analysis system 1000 is described. In a prior step 1010, the agricultural land 120 is measured both: (1) spatially and (2) spectroscopically. Generally, an m×n matrix of cropland areas are measured, where m and n are positive integers, such as greater than 10, 50, 100, 500, 1,000, 5,000, or 10,000, where the size of the m×n matrix optionally relates to pixels in an associated two-dimensional detector, described supra. More particularly, as illustrated, a spatially resolved first position, $P_1$, 1021 and second position, $P_2$, 1022 of the agricultural land 120 are remotely monitored, yielding a first response vector 1031 and a second response vector 1032, respectively. The two crop areas, identified as the first position 1021 and the second position 1022, illustrate regions that require treatment. In this case six spectral responses are illustrated of x wavelengths, where x is a positive integer of at least 3, 5, 10, 15, 25, 50, 100, or 1000. A first iterative step of using a model 1040 to analyze the spatially resolved spectral responses shows that: (1) the first response vector 1031 reveals three outlier responses, denoted with thicker lines, indicative of a first required treatment and (2) the second response vector 1032 reveals a different three outlier responses indicative of a second required treatment. Calibration 1042 of the model 1040 is further described, infra. A second iterative step of treating 1050 the agricultural land 120 is performed. As illustrated, a first treatment, $T_1$, 1061 of applying water and pesticide to the first position 1021 is performed based on the near-infrared water absorbance signals and mid-infrared temperature signals, as described supra. Similarly, a second treatment, $T_2$, 1062 of applying water and fertilizer to the second position 1022 is performed based on the visible and near-infrared water absorbance signals, as described supra. A third iterative step of dynamically measuring 1070 updates information on previously treated positions and/or identifies new positions requiring treatment. In the first dynamic update illustrated: (1) the first position 1021 indicates a successful treatment; (2) a fourth response vector 1034, an update of the second response vector 1032, indicates that watering the second position 1024 was successful, but more fertilizer is required; and (3) a third position, $P_3$, is now identified that requires treatment. The iterative steps of using the model 1040 to generate a recommended treatment, treating 1050 the identified positions, and updating measurement by way of the step of dynamically measuring 1070 are optionally and preferably repeated at least daily, two, three, or more times a week, weekly, every other week, and/or monthly season after season. To perform this with satellites, a constellation of greater than 5, 10, 25, or 50 satellites is optionally and preferably used. The calibration step 1042 uses known and/or reference measurements to calibrate the multivariate model 1040.

Figure 11A:
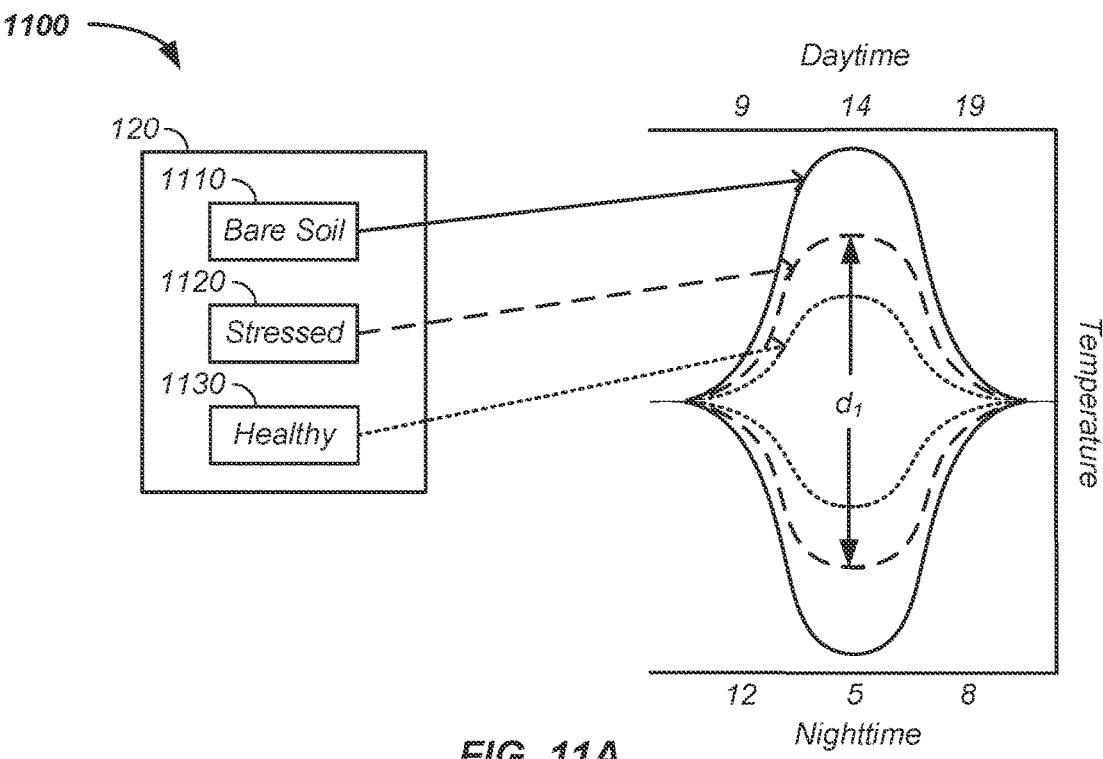
FIG. 11A and FIG. 11B illustrate a temporally updated wavelength and spatially resolved agricultural monitoring system.
Figure 11B:
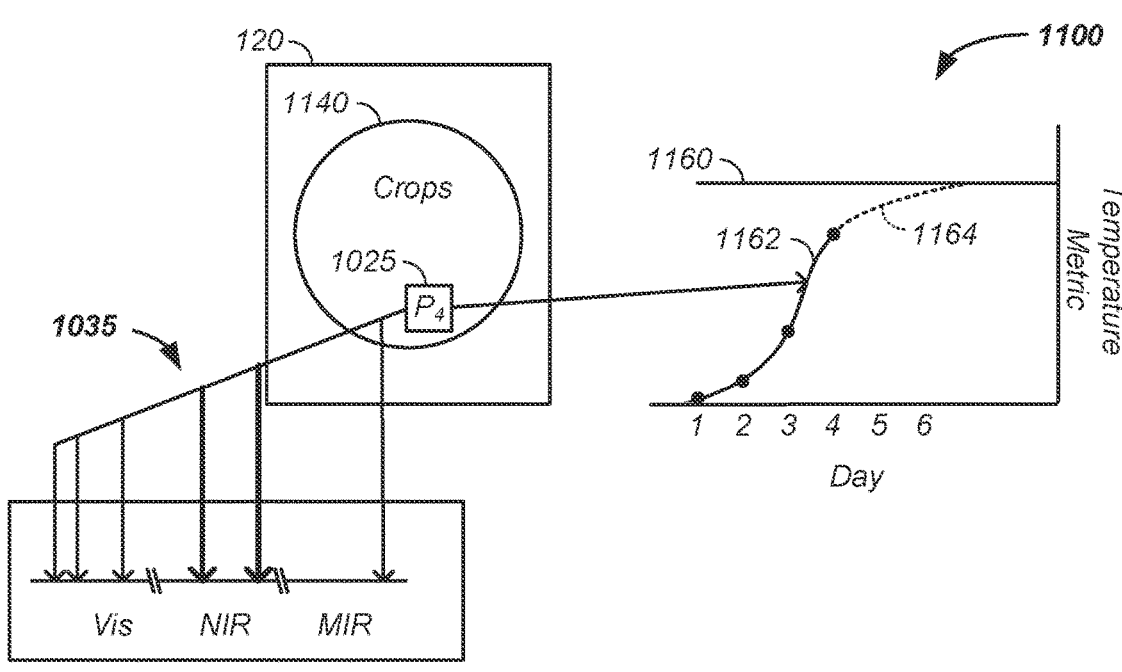

Referring now to FIG. 11A and FIG. 11B a first example of crop health analysis 1100 is provided. The crop health analysis 1100 example illustrates calibrating a model, acquiring measured data, applying the model to the measured data, and repeating the iterative process as a function of time to yield information on a given position of the agricultural land 120. Particularly, as illustrated, spectral responses from the visible, near-infrared, and infrared measurement systems on the satellites 115 are correlated with reference information, such as the state of the agricultural land 120 being bare soil 1110, stressed crops 1120, or healthy crops 1130. For clarity of presentation and without loss of generality, a particular relationship between temperature as a function of time of day relative to condition of a location of the agricultural land 120 is illustrated. As illustrated, the temperature of bare soil 1110, healthy crops 1130, and stressed crops 1120, adjusted for weather conditions and weather history, reaches a maximum temperature in the afternoon, such as at two o'clock post meridiem. However, the peak temperature of the healthy crops 1130 is less than the bare soil 1110 and as the crops are increasingly stressed 1120, the peak temperature departs from the peak temperature of the healthy crops 1130 and increases toward the peak temperature of the bare soil 1110. Thus, a quantitative measure of crop stress results. Naturally, any combination of wavelengths, ratios, and/or analytical approaches are used to find, determine, and/or use correlations/relationships of differing degrees of plant stress with the satellite gathered data. Referring now to FIG. 11B, a fourth position, $P_4$, 1025 of a crop sub-area 1140 of agricultural land 120 yields a fifth response vector 1035, determined by the model 1040 to have a measure of crop stress, such as related to hydration. Using the iterative crop analysis system 1000, described supra, the measure of crop stress 1162 is observed to increase as a function of time, such as over a course of days, toward a previously determined stress threshold 1160, such as a first visual sign or crop stress. Further, as illustrated, the model 1040 prognosticates that the crop at the fourth position 1025 will reach the stress threshold 1160 in two days if not treated according to the recommended treatment provided by the model 1040 using the fifth response vector 1035.

Still referring to FIG. 11A and FIG. 11B a second example of crop health analysis 1100 is provided. The crop health analysis 1100 example above illustrates calibrating a model, acquiring measured data, applying the model to the measured data, and repeating the iterative process as a function of time to yield information on a given position of the agricultural land 120. In this example, a differential analysis is used to compensate/normalize parameters that affect temperature, such as cloud cover, humidity, solar activity, and/or percent of crop cover. Particularly, as illustrated, spectral responses from the visible, near-infrared, and infrared measurement systems on the satellites 115 are correlated with reference information, such as the state of the agricultural land 120 being bare soil 1110, stressed crops 1120, or healthy crops 1130 are optionally recorded overnight. As illustrated, the temperature of bare soil 1110, healthy crops 1130, and stressed crops 1120, reaches a minimum temperature in the early morning, such as at five o'clock ante meridiem. However, the minimum temperature of the healthy crops 1130 is greater than the bare soil 1110 and as the crops are increasingly stressed 1120, the minimum temperature departs from the minimum temperature of the healthy crops 1130 and decreases toward the minimum temperature of the bare soil 1110. Thus, a second quantitative measure of crop stress results. As outside parameters affect daytime and nighttime temperatures a form of a normalized adjusted temperature is a differential temperature, di, between a daytime reading, such as a high temperature, and a nighttime reading, such as a low temperature, where the differential temperature is a third metric. Referring again to FIG. 11B, the temperature metric optionally refers to the second metric and preferably refers to the third metric due to an internal adjustment for outside temperature adjusting parameters.

In another example, crop type and crop growth as a function of time are used to further aid development of a recommended treatment for each location as a function of time using multi-wavelength band spectral data. The crop type and crop growth information is optionally provided; however, preferably the crop type and crop growth stage is determined using the remote agricultural monitoring system 100. For instance, the crop is identified as corn or soybean. Further, a post-sprout age of the crop is determined using the remote agricultural monitoring system 100. As treatment requirements for a first crop type, such as corn, differs as a function of time, such as 6 or 12 weeks post-sprout, and as treatment requirements for the first crop type differ from a second crop type, such as soybeans, the recommended treatment 1050 provided by the model 1040 is optionally and preferably adjusted by a basis set database for the identified crop and identified time period in the crop life.

Generally, the model 1040, using calibration data 1042, operates on an initial prior measurement 1010/one-time measurement and/or a dynamically updated measurement 1070 to generate a recommended treatment 1050, using a spectral response vector, for one or more positions of the agricultural land 120. The response vector input to the model 1040 is optionally and preferably supplemented with one or more of:

- soil measurements/type, such as clay, sand, or organic optionally as a function of depth;
- weather reports: historical, current, and/or forecast;
- solar reports: UV index, elevation, sun spots;
- soil treatment history: amendments, pesticide use, herbicide use, fertilizer use;
- topography;
- pest history/projection;
- invasive species history/projection: plant and/or animal; and
- a projected harvest date, to avoid crop treatment residual on harvest.

In another example, one or more satellites orbit the planet in low, medium, and/or high orbits, where each satellite is designed to enable acquisition of remote sensing information with high spatial resolution and high temporal resolution. Ground spatial resolution of ten meters or less is used to identify features in sub-regions within agricultural fields containing either healthy crops or crops under stress. Temporal resolution comprises satellite revisits over the same geographical region on a daily basis or better to provide information to decision makers, such as farmers, to make important decisions to apply the necessary resources to mitigate problems detected in these regions. Satellites are optionally arranged in a constellation to enable high temporal resolution of daily revisits or better by satellites at the same ground location. The acquired remote-sensing data is optionally processed onboard each satellite to generate data and information products for dissemination to appropriate consumers within less than 6, 12, 24, 36, or 48 hours from the time of data acquisition.

In another example, after the remote agricultural monitoring system 100 gathers information with a satellite 115, such as at a first resolution, optionally a secondary system is used to further map identified trouble areas and/or areas with highly variable treatment recommendations. For instance, if an entire area calls for fertilizer, then a second higher resolution analysis is not necessarily necessary. However, if the satellite 115 results reveal a patchwork of treatment recommendations, such as varying on the order of the resolution of the satellite data, then the secondary system, such as the airplane 114 or a drone, is used to further map, enhance the existing map, and/or remap the identified patchwork area. As the drone altitude is substantially less than the satellite, enhanced spatial resolution is made possible and can be made with some intermittent interferences, such as clouds. The inventor notes that optionally copies of the spectrometers mounted on the satellite 115 are used on the drone resulting in enhanced spatial resolution, due to the lower altitude of the drone. Further, the identical copies or identical sub-element copies of the satellite analyzers greatly reduces complexities of designing, developing, and implementing the data collection hardware and/or greatly reduces complexities of merging a first data cube from the satellite 115 with a second data cube from the drone due to similarities of baselines, noise characteristics, response curves, and/or any spectra altering hardware element of the analyzer.

In still another example, remote sensing is performed at one or more electromagnetic wavelength bands such as the visible, near-infrared, mid-infrared, long wavelength infrared, microwave, and/or radio bands. Sensors onboard satellites acquire point measurements and preferably imaging measurements of the planetary surface locations. Different kinds of information are acquired from each of the above-mentioned electromagnetic spectral bands. For example, the -visible and near-infrared bands allow determination of coverage of the land surface by vegetation or bare soil, mid-infrared wavelength bands allow determination of atmospheric moisture content, long wavelength infrared measurements allow determination of the land surface temperature both of vegetation and soil, and microwave and radio bands allow measurements of the soil moisture content as well as the refractive index of the atmosphere.

In yet another example, specialized communication protocols are used for optimizing the rapid uplink and downlink of information to and from the orbiting satellites from ground transmission/receiving stations. High-speed processing of acquired information onboard the orbiting satellites in a near real time manner is optionally and preferably used to generate derived information products, such as those described above. Further, specialized algorithms for the efficient processing of the acquired information and generating derivative information products are used in conjunction with methods for rapid dissemination of data and derivative information products within 24 hours of remote-sensing acquisition. Thus, large data sets, the raw data cubes, are analyzed to generate actionable results, which are optionally and preferably rapidly transmitted, such as to an end-user, an end-user cellphone/computer, and/or an electromechanical farm implement.

In still another example, information derived from the satellite based remote sensing system is provided to one or more autonomous and/or semi-autonomous agricultural implements and/or systems, such as to a fertilizer, herbicide deployment system, pest reducer, irrigator, crop inspector, and/or harvester, where the information is direct sent to the agricultural implements and/or indirectly sent to the agricultural implements.

NDVI

Normalized difference vegetation index (NDVI) is a vegetation index. A formula for NDVI is provided in equation 1, $$NDVI = (NIR - R)/(NIR + R) \qquad \text{eq. (1)}$$

where NIR is a measure of leaf reflectance in the near-infrared (NIR) region and leaf reflectance in the red region. Generally, the near-infrared region is a measure of leaf reflectance scatted by mesophyll structures of leave and the red region is a measure of chlorophyll, which absorbs red light making healthy leaves appear green. The normalized difference vegetative index is a predictor of plant health and plant productivity and is a measure of standing biomass. Traditionally, very narrow NDVI readings of 614 and 665 nm are used to measure the red chlorophyll and 833 and 855 nm are used to measure the near-infrared mesophyll structures. As discussed, infra, the inventor has determined that many different and/or additional wavelengths are optionally used in a new normalized difference vegetative index, where the red and near-infrared wavelengths differ from the standard 614, 665, 833, and 855 nm wavelengths. Indeed, the wavelengths are optionally in the mid-infrared region of 2500 to 8000 nm and/or the short thermal infrared wavelengths of 5000 to 12,000 nm, described supra.

Figure 12:
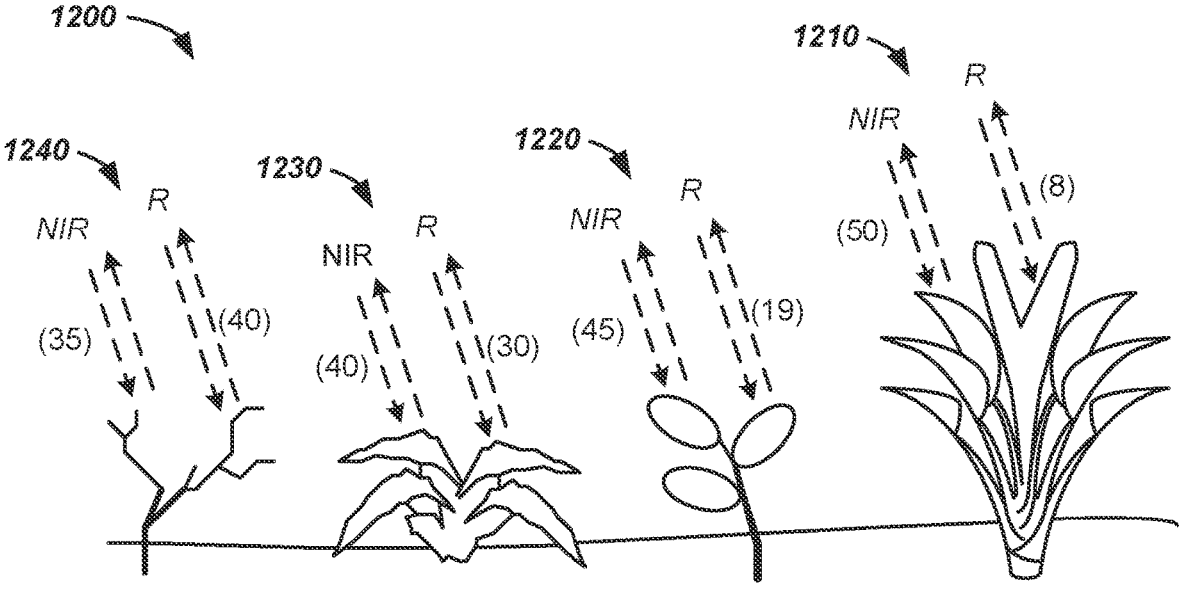
FIG. 12 illustrates normalized difference vegetative index readings.

Referring now to Table 3 and Figure and FIG. 12, NDVI as a measure of plant condition is described. Generally, as the plant condition decreases, the NDVI decreases. As seen in Table 3, a very healthy plant has an NDVI of 0.66 to 1.0, a moderately healthy plant has an NDVI of 0.33 to 0.66, an unhealthy plant has an NDVI of 0 to 0.33 and a dead plant has an NDVI of −1 to 0. FIG. 12 illustrates plant conditions 1200 with exemplary red and near-infrared readings for very healthy 1210, moderately healthy 1220, unhealthy 1230, and dead 1240 plants.

TABLE 3

| NDVI and Plant Condition | |
| --- | --- |
| NDVI | Plant Condition |
| 0.66 to 1 | Very Healthy |
| 0.33 to 0.66 | Moderately Healthy |
| 0 to 0.33 | Unhealthy |
| −1 to 0 | Dead |

Still referring to Table 3 and FIG. 12, NDVI is readily used in a pixel-wise calculation, where pixels correspond directly and/or indirectly to image pixels collected from satellite observatories, such as those monitoring cropland. The pixel-wise calculations optionally and preferably correlate to resolution of the cropland analysis, such as at highest magnification. Thus, for NDVI alone, measures of red light and near-infrared light yield, spatially resolved, are a measure of crop health, where NDVI is optionally tracked temporally through time. As further described herein, additional wavelengths outside of the red and near-infrared light are optionally and preferably used to enhance the measure of the crop condition. As further described, infra, wavelengths within the visible and/or infrared region are optionally used to yield more detailed information about the crop condition, such as through a measure of water, temperature, protein, and/or fat. As described, supra, NDVI is optionally and preferably combined with additional information, such as uploaded localized precipitation, temperature history, forecasted precipitation, forecasted temperature, localized pest information, and/or applied fertilizer information.

Example I

Figure 13:
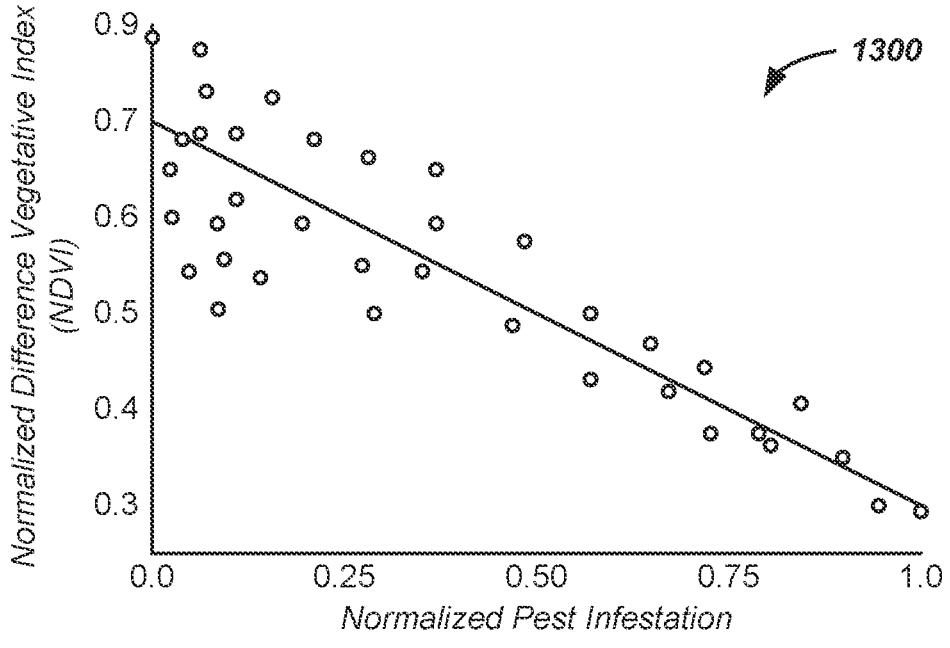
FIG. 13 illustrate pest infestation as measured by NDVI.

Referring now to FIG. 13, a first example of NDIV use is illustrated. For spatially resolved regions, NDVI is plotted against pest infestation 1300. As observed, for this normalized measure of pest infestation of number of stems infested and insects per stem, as the pest infestation increases to a maximum from a minimum, the NDVI decreases from about 0.7 to about 0.3. Indeed, for a variety of crop species, such as cotton, soybean, corn, and wheat, infested plants, such as infested by aphids, mites, and/or a herbivore show decreasing NDVI numbers relative to a similarly time developed uninfested crop. Thus, on-board the satellite, the NDVI is calculated for each spatially resolved region and for at least some infested regions, as measured by NDVI, the result of pest infestation is transferred to the farmer, such as via the base station 130. Further, based on nearby spatially resolved areas showing higher pest infestation, weather, wind direction, wind speed, water content in the air, moisture on the ground, and/or temperature, the NDVI measure is optionally improved and projected in the form of a model prediction to prognosticate a pest infestation for downwind spatially resolved areas of cropland having beneficial temperature and/or water conditions conducive to spreading/growth of pests, such as puparia.

Example II

The red of the NDVI is optionally measured at any red wavelength in the visible region, any two wavelengths in the visible region, and/or at any three or more wavelengths in the visible region. Indeed, the 1, 2, 3, or more wavelengths are optionally any visible wavelengths from 400 to 700 nm. The wavelength regions are optionally separated by greater than 1, 2, 10, 20, or 50 nm. Similarly, the near-infrared region is optionally measured at 1 or more wavelengths, such as greater than 1, 2, 3, or more wavelengths in a region of 700 to 100 or 700 to 2500 nm. Again, the wavelength regions are optionally separated by greater than 1, 2, 10, 20, or 50 nm. For instance, in measurement of the Hessian fly, examples of red wavelengths include 614±30, 50, 70, or 90 nm; 665±20, 40, or 60 nm; or a red wavelength with a bandpass of about 10, 20, 40, or 70 nm. Similarly, in the measurement of the Hessian fly, examples of NIR wavelengths include 833 nm and 855 nm with bandpasses of less than 10, 20, 50, 100, or 200 nm.

Figure 14A:
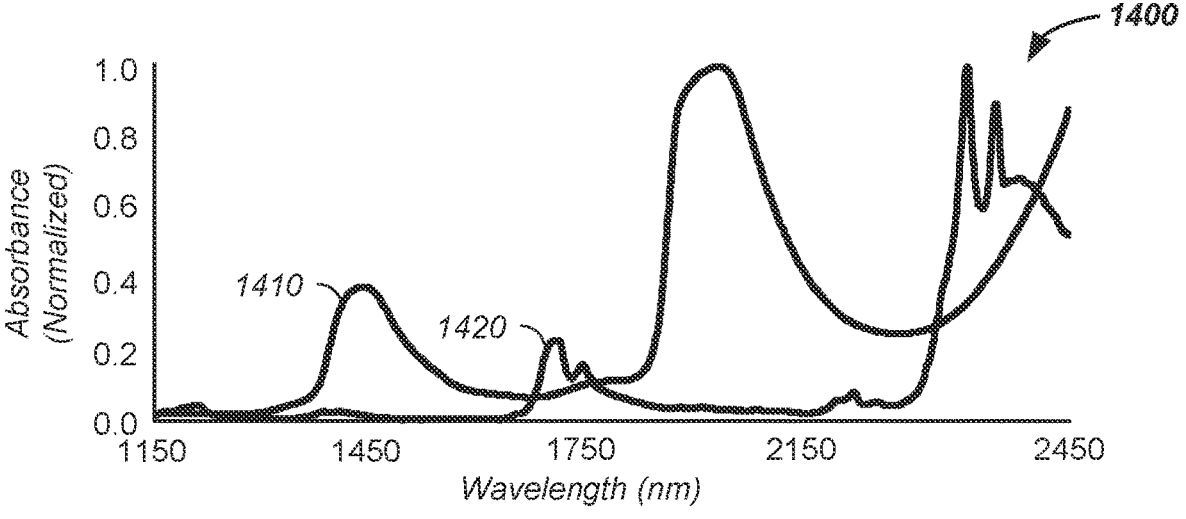
FIG. 14A illustrates water and fat absorbance and FIG. 14B illustrates fat and protein absorbance.
Figure 14B:
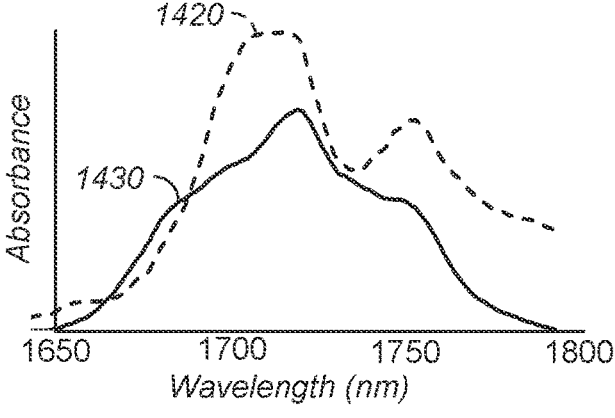
Figure 15:
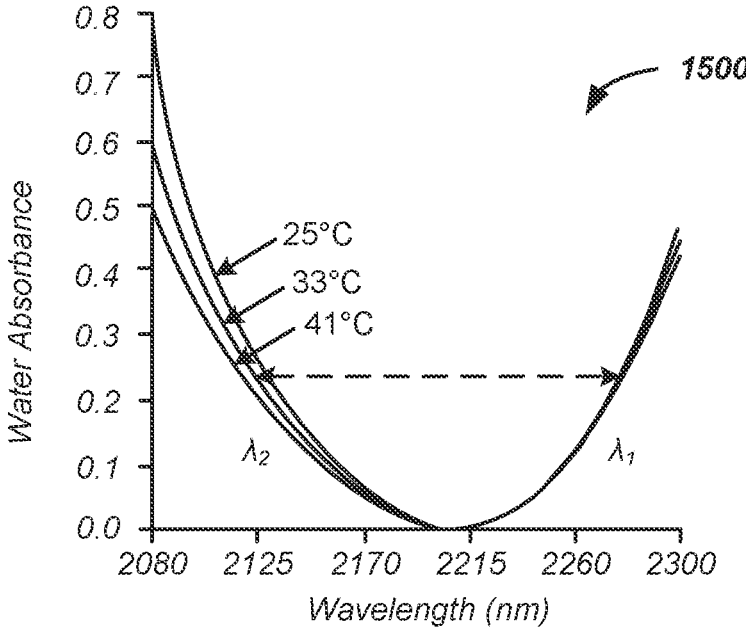
FIG. 15 illustrates water protein absorbance.

Referring now to FIG. 14A and FIG. 14B, additional wavelengths tied to different spectral features are used to measure crop infestation. Bio-chemical spectra 1400, such as water absorbance 1410, fat absorbance 1420, and/or protein absorbance 1430 bands are optionally used to track/prognosticate crop condition. For instance, severe pest infestations and/or high resolution images, such as individual plants, are identified from protein absorbance of the herbivores, such as at 1690 nm, and/or from the fat absorbance at 1715 nm. For instance, treatment of even individual corn stalks is possible with sufficient resolution. Similarly, referring now to FIG. 14A and FIG. 15, water absorbance is optionally used to determine a concentration of water present and/or a temperature of the crop. For instance, water in the crops is readily measured using water absorbance maxima within any of the ranges of 1400 to 1600 nm, 1800 to 2100 nm, and 2300 to 3000 nm. Similarly, temperature of the crops and/or the surrounding soil is readily measured using differences in absorbance at two or more wavelengths. For instance, referring now to FIG. 15, a first absorbance is measured at a wavelength showing little to no shift with temperature, such as at 2215 to 2300 nm and a second absorbance is measured at a water absorbance wavelength that is temperature dependent, such as from 2000 to 2180 nm. As illustrated, when the absorbance is measured at 2275 nm and 2125 nm, a lower absorbance at 2125 nm, relative to 2275 nm, indicates a temperature from 33 to 41° C. and a higher absorbance at 2125 nm indicates a temperature from 33 to 25° C., where the temperature is further resolved as a measure of the difference, such as to a temperature reading of less than 5, 2, 1, 0.5, or 0.2° C. More generally, a temperature dependence of a wavelength shift of water is used to measure the crop temperature, the soil temperature, and/or the ambient temperature of the cropland. This measurement is aided by water being a dominant absorber of crops in the wavelength range of 1350 to 3000 nm.

Several additional examples are provided to help describe on-board satellite processing.

Example I

In a first example, the satellite optionally and preferably processes temporal images and spatial images on-board the satellite. Information from any of the spectral regions described herein are optionally shared with other satellites before communication of an analysis results or model result down to the base station. On-board the satellite, a first spectral library is optionally used to identify a crop type for a given spatial location, a second spectral library is used determine a degree of pest infestation, a third spectral library is used to determine a stage of crop development, and/or a fourth spectral library is used to determine a degree of crop development. Similarly, comparisons of crop images at different times are optionally used, with or without any of the libraries, to determine a stage of crop development versus an expected crop development. Any of the library information is optionally at any of the wavelength ranges described anywhere herein.

Example II

In a second example of on-board satellite processing, at a first time a crop is observed to sprout. As a second time, a fifty percent drop development is expected to observed, as maintained on-board the satellite, such as in a look up table and/or as a measure, such as temperature, color, and/or water absorbance. On-board the satellite, the observed crop condition is measured against the expected crop development at the fifty percent time, where 50% is merely an example of any time, such as from 1 to 100 percent crop development, such as at about 10, 20, 30, 40, 50, 60, 70, 80, or 90±1, 2, 4, 6, or 8 percent. Certainly, the amount of image data collected by the satellite over a exemplary 100 day growing cycle from images collected up to 24 hours a day using 1, 2, 3, or more spectrometers is immense. The on-board satellite processing reduces the size of the downloaded/processes/modeled data by in excess of 10, 20, 40, 60, 80, 90, 95, 99, or 99.9 percent.

Example III

In a third example of on-board satellite processing, differential measurements/comparisons are made. For instance, differences in a given area are observed, such as day-to-day, week-to-week, and/or of n-days different, such as where n is 1 to 100 days at any interval number of days or hours. Again, any wavelength range described herein is optionally used as is any spectral library and/or any uploaded information to yield a current crop state determination and/or to yield a crop state prognostication, such as for the upcoming 1, 2, 3, 4, 5, 6, 7 or more days, and/or to yield a recommended crop treatment, such as watering, fertilizing, and/or a pest mitigation process, such as a recommended application of a pesticide.

Example IV

In a fourth example, on-board the satellite, information is optionally and preferably fused. For instance, the temporal and/or spatial images, from any spectral range, are optionally and preferably further analyzed in view of uploaded information, such as a weather forecast, wind speed, wind directions, temperature, humidity, and/or a neighbor's crop report, such as a pest infestation, to yield a prediction, such as a future crop infestation, such as within the next 1, 2, 3, 4, 5, 6, or 7 days.

Example V

In a fifth example, on-board the satellite, many spectral bands are optionally analyzed, such as with resolutions of less than 100, 50, 20, or 10 nm over a range of the respective spectrometer, such as in the visible, near-infrared, and thermal infrared regions described above. Optionally and preferably, one or more of the spectrometers collects spectral information every 1, 2, 5, 10, or 20 nm across the spectral range of the analyzer.

Example VI

Optionally and preferably, carbon dioxide ($CO_2$) is optionally measured by the orbiting satellite, such as at absorbance bands centered at about 2000, 2700, 4300, and/or 15,000 nm.

Figure 16:
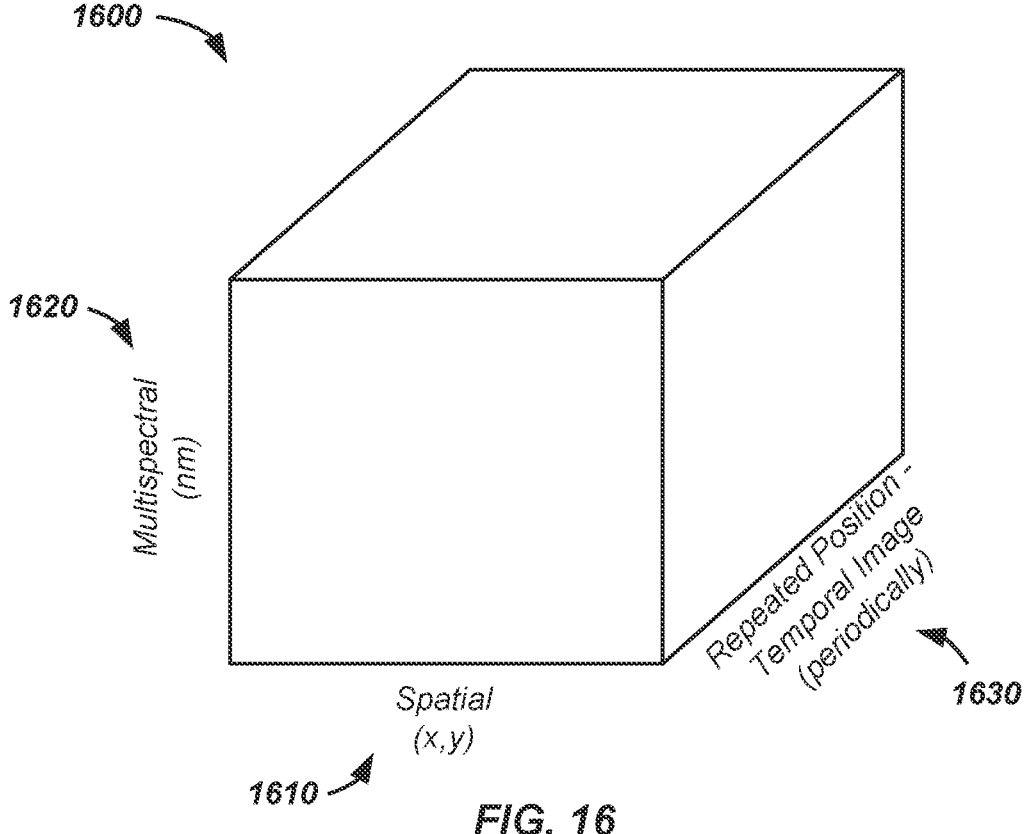
FIG. 16 illustrates an n-dimensional data cube.

Referring now to FIG. 16, an n-dimensional data cube 1600 is illustrated, such as collected by the orbiting satellite 115. Generally, imaging data 1610 is collected, such as along an x- and/or a y-axis. The position of the imaging data 1610 on earth moves as the satellite 115 orbits the earth. Optionally for many and preferably for each x/y-position of imaged area, one or more spectrometers collect intensity/current/voltage signals, such as a measure of reflected light and/or as a measure of emitted light, which are optionally represented as absorbances. For instance, any one or more of the spectral ranges, or ranges therein, described infra, are collected for each x/y-position of the satellite. Optionally and preferably multispectral readings 1620, readings over two or more wavelength regions, are collected for each imaged x/y-position. As the satellite moves, readings are also collected as a function of time. However, more specifically, images for a previously imaged x/y-position are optionally and preferably collected again and again as a function of time, referred to herein as a repeated position-temporal image 1630. Optionally and preferably, representations of the n-dimensional data cube, with or without repeated position-temporal images, are reduced in size/analyzed on board the satellite 115, as described supra.

Figure 17:
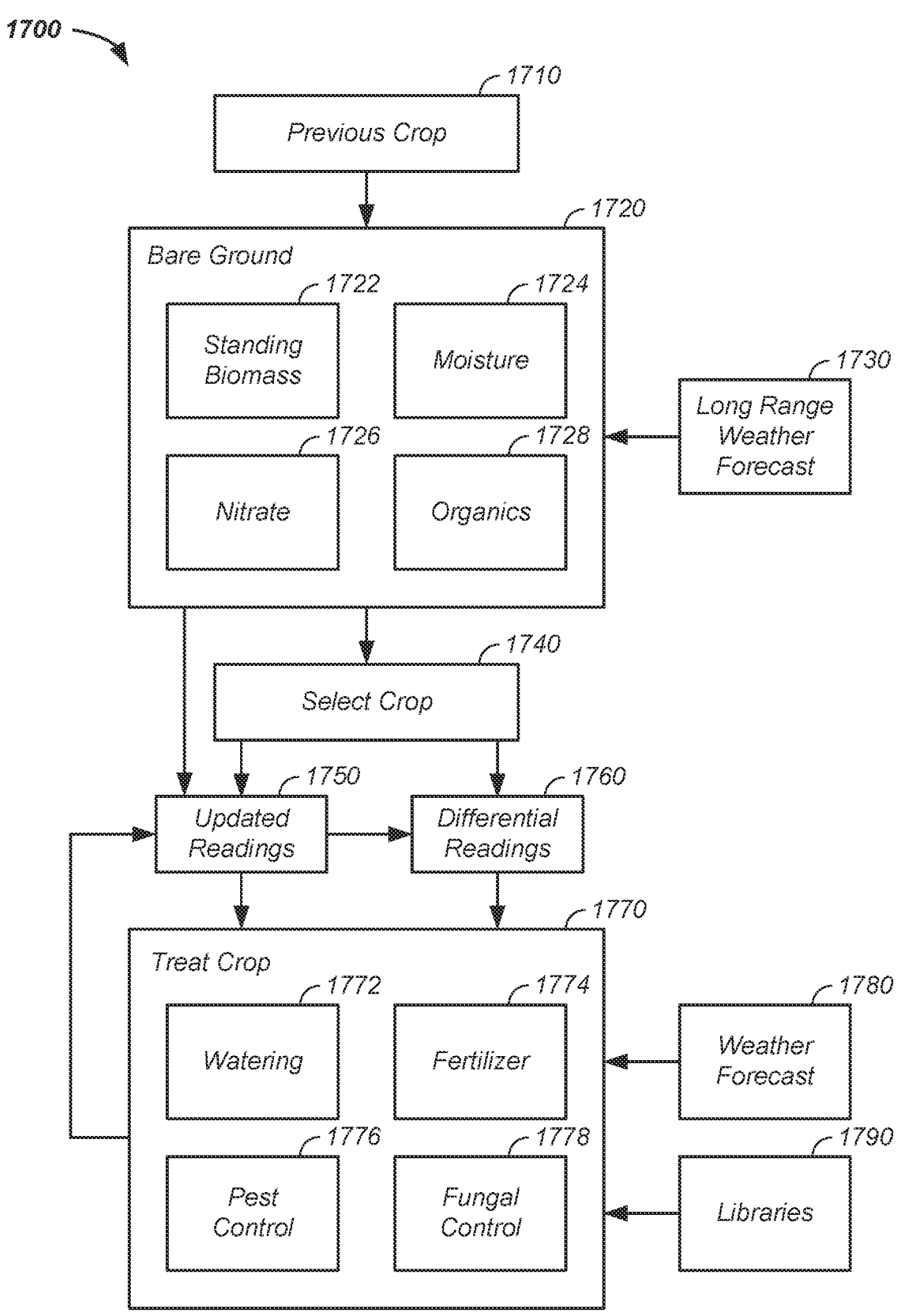
FIG. 17 illustrates a crop selection/monitoring tool.

Referring now to FIG. 17, a crop selection/crop monitoring tool 1700 is presented.

Still referring to FIG. 17, in a first optional step, a previous crop 1710 is identified. The previous crop, for a given spatial x/y-position, is optionally provided as an upload to the orbiting satellite 115 and/or is a stored result from a previous analysis of the crop, with or without use of a crop type library, of the previous position. The usefulness of knowing the previous crop is illustrated with crop rotation. In crop rotation, uptake and replenishment of chemicals, such as nitrogen fixation by soybeans in a corn-soybean crop rotation, is used to benefit subsequent crops and/or is used to control pests, by interrupting their food supply. Similar crop rotations are a broccoli, winter wheat, sweet corn rotation and a wheat, fallow, alfalfa, potato rotation or subsets thereof. Similarly, grass, clover, alfalfa, and manure applications are measures of treatment of the land biochemically for a subsequent crop. Thus, identification of a previous crop 1710, on-board the satellite 115, provides a first set of chemical, pest, and/or fungus information, which is then applied to knowledge of selecting a crop type, planting the crop, and monitoring the crop, as further described infra. For instance, in a high water content year, water thirst drops such as rice, soybeans, wheat, sugarcane, cotton, and/or alfalfa are optionally planted.

Still referring to FIG. 17, a bare ground 1720 reading by the satellite 115 is optionally and preferably performed, such as just after harvest, during an off-season, just before planting, and/or after planting up until early sprouting. The bare ground analysis yields a set of readings/land condition state information. For example, standing biomass 1722 is optionally and preferably measured with a green color, such as a red absorbance, as described supra, a measure of brown/black coloration of the soil, and/or via a metric, such as percent green cover and/or and NDVI type reading. Generally, the standing biomass 1722 provides a measure of carbon biomass/fertilizer for a subsequent crop along with a measure of stored water. Similarly, the bare ground 1720 is optionally analyzed spectrally for moisture 1724, such as a water content, such as via use of a water absorbance or lack thereof in the near-infrared region. Knowledge of the water content in the soil is optionally supplemented/enhanced via use of a water content spectral library of soil with different amounts of moisture, such as a library maintained on the orbiting satellite 115. The analysis 440 is optionally enhanced with an upload of a long range weather forecast 1730, such as a La-Nina or El-Niño forecast, which indicates more or less rainfall for entire regions, such as the desert southwest of America. Similarly, the bare ground 1720 is readily measured for nitrates ($NO_3^-$), which is a measure of nitrogen, such as at 1320 nm (7602 $cm^{-1}$) and/or for ammonia ($NH_3$), also a measure of nitrogen, with absorbances at 950 $cm^{-1}$, 1628 $cm^{-1}$, and/or 3300 $cm^{-1}$, and/or with overtones and/or combinations thereof. Similar measures are available for various bio-chemical/organic chemicals/compounds, such as carbohydrates, lipids, protein, and/or nucleotides. Based upon the measures of in-place fertilizers, moisture, and/or predicted weather, the on-board processor 730 optionally generates a recommended/selected crop type 1740.

Still referring to FIG. 17, updated readings 1750, such as any of the readings described supra, and/or differential readings 1760, such as any of the readings described supra, are optionally and preferably repeatedly taken for a given spatial area and used to provide suggested crop treatments 1770, such as watering 1772, fertilizing 1774, application of a pest control 1776 substance/action, and/or recommendation for timing/type of a fungal control 1778. As above, the on-board processing is optionally and preferably supplemented with outputs of a weather forecast 1780, such as a short term, 1, 2, 3, 4, 5, 6, 7, . . . , 14 day weather forecast and/or the use of any of the libraries 1790 described herein. Herein, differential readings 1760 are optionally calculated differences between two observed spectra collected at different times and/or are comparisons made against a library result. For instance: (1) reflectance is measured in the 8,000 to 12,000 nm region during the day and emittance is measured in the 8,000 to 12,000 nm region at night and/or (2) differential measures of growth are taken as a function of time, such as related to an earlier measurement or against a spectral library of expected growth.

Still yet another embodiment includes any combination and/or permutation of any of the elements described herein.

The main controller, a localized communication apparatus, and/or a system for communication of information optionally comprises one or more subsystems stored on a client. The main controller is optionally and preferably linked directly, indirectly, and/or wirelessly to one or more electromechanical devices, such as instrumentation and computing elements. The client is a computing platform configured to act as a client device or other computing device, such as a computer, personal computer, a digital media device, and/or a personal digital assistant. The client comprises a processor that is optionally coupled to one or more internal or external input device, such as a mouse, a keyboard, a display device, a voice recognition system, a motion recognition system, or the like. The processor is also communicatively coupled to an output device, such as a display screen or data link to display or send data and/or processed information, respectively. In one embodiment, the communication apparatus is the processor. In another embodiment, the communication apparatus is a set of instructions stored in memory that is carried out by the processor.

The client includes a computer-readable storage medium, such as memory. The memory includes, but is not limited to, an electronic, optical, magnetic, or another storage or transmission data storage medium capable of coupling to a processor, such as a processor in communication with a touch-sensitive input device linked to computer-readable instructions. Other examples of suitable media include, for example, a flash drive, a CD-ROM, read only memory (ROM), random access memory (RAM), an application-specific integrated circuit (ASIC), a DVD, magnetic disk, an optical disk, and/or a memory chip. The processor executes a set of computer-executable program code instructions stored in the memory. The instructions may comprise code from any computer-programming language, including, for example, C originally of Bell Laboratories, C++, C#, Visual Basic® (Microsoft, Redmond, WA), Matlab® (MathWorks, Natick, MA), Java© (Oracle Corporation, Redwood City, CA), and JavaScript® (Oracle Corporation, Redwood City, CA).

Herein, any number, such as 1, 2, 3, 4, 5, is optionally more than the number, less than the number, or within 1, 2, 5, 10, 20, or 50 percent of the number.

Herein, an element and/or object is optionally manually and/or mechanically moved, such as along a guiding element, with a motor, and/or under control of the main controller.

The particular implementations shown and described are illustrative of the invention and its best mode and are not intended to otherwise limit the scope of the present invention in any way. Indeed, for the sake of brevity, conventional manufacturing, connection, preparation, and other functional aspects of the system may not be described in detail. Furthermore, the connecting lines shown in the various figures are intended to represent exemplary functional relationships and/or physical couplings between the various elements. Many alternative or additional functional relationships or physical connections may be present in a practical system.

In the foregoing description, the invention has been described with reference to specific exemplary embodiments; however, it will be appreciated that various modifications and changes may be made without departing from the scope of the present invention as set forth herein. The description and figures are to be regarded in an illustrative manner, rather than a restrictive one and all such modifications are intended to be included within the scope of the present invention. Accordingly, the scope of the invention should be determined by the generic embodiments described herein and their legal equivalents rather than by merely the specific examples described above. For example, the steps recited in any method or process embodiment may be executed in any order and are not limited to the explicit order presented in the specific examples. Additionally, the components and/or elements recited in any apparatus embodiment may be assembled or otherwise operationally configured in a variety of permutations to produce substantially the same result as the present invention and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present invention, in addition to those not specifically recited, may be varied or otherwise particularly adapted to specific environments, manufacturing specifications, design parameters or other operating requirements without departing from the general principles of the same.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. A method for managing cropland for a client, comprising the steps of:

optically measuring, each of a set of spatially resolved locations, level zero data with an orbiting satellite, said level zero data comprising:

first reflected cropland radiation, in a visible range of 400 to 1,000 nm;

second reflected cropland radiation in a near-infrared range of 1,000 to 3,000 nm;

third radiation in a range of 3,000 to 5,000 nm; and emitted radiation, in a thermal infrared range of 8,000 to 12,000 nm;

processing, on-board said orbiting satellite, said level zero data comprising a first data storage size, to yield cropland condition information comprising a second data storage size of less than one percent of said first data storage size;

receiving from said orbiting satellite to a ground-based communication system said cropland condition information;

relaying at least a portion of said cropland condition information to the client within twenty-four hours; and inter-crop measuring, after harvest and prior to subsequent crop sprouting, crop soil characteristics of a piece of land with said orbiting satellite.

2. The method of claim 1, further comprising the step of:

determining an immediately previous crop type for a piece of land, said step of determining an immediately previous crop type further comprising at least one of the steps of:

uploading to said orbiting satellite an immediately previous crop type for the piece of land; and previously determining, on-board said orbiting satellite, said immediately previous crop type for the piece of land.

3. The method of claim 2, further comprising the steps of:

collecting said first reflected cropland radiation with a silicon detector;

collecting said second reflected cropland radiation with an indium-gallium-arsenide detector;

collecting said third radiation with an indium-phosphide detector; and collecting said emitted radiation with a gallium-antimony detector.

4. The method of claim 2, further comprising the step of:

uploading a seasonal weather prediction to said orbiting satellite.

5. The method of claim 1, further comprising the step of:

measuring water absorbance of said piece of land with both said indium-gallium-arsenide detector and said indium-phosphide detector.

6. The method of claim 5, said step of measuring water absorbance further comprising the step of:

adjusting said water absorbance at a wavelength greater than 1850 nm and less than 2170 nm with a second water absorbance reading at greater than 2230 nm and less than 3000 nm.

7. The method of claim 5, further comprising the step:

determining coverage of standing biomass of the piece of land with said silicon detector.

8. The method of claim 7, said step of determining coverage further comprising the step of:

measuring a red absorbance of said piece of land.

9. The method of claim 7, further comprising the step of:

determining an amount of stored water in the piece of land with a red reading from said silicon detector and a comparison to water storage as a percent of standing biomass in a set of library spectra with known water storage as a function of red readings, said library spectra maintained on-board said orbiting satellite.

10. The method of claim 9, further comprising the step of:

indirectly determining a nitrogen concentration present in a crop of the immediately previous crop type of the piece of land with at least one of:

a measure of nitrate at 1320 nm with said indium-gallium-arsenide detector;

a measure of ammonia at 3300 cm$^{-1}$ aboard said orbiting satellite;

indirectly measuring nitrogen through a measure of red light with said silicon detector; and receiving an upload to said orbiting satellite of an amount of applied fertilizer.

11. The method of claim 10, said step of processing further comprising the step of:

recommending a plant type to plant on the piece of land based on at least two of:

said immediately previous crop type;

readings taken from said orbiting satellite during a time period of said inter-crop measuring;

said amount of stored water; and said determined nitrogen concentration.

12. The method of claim 11, further comprising the step of:

measuring an amount of water associated with the piece of land with said orbiting satellite; and said step of processing performing said step of recommending with inclusion of said amount of water.

13. The method of claim 12, further comprising the step of:

monitoring after planting the recommended plant type, on-board said orbiting satellite, the piece of land with each of:

a silicon detector;

an indium-gallium-arsenide detector;

an indium-phosphide detector; and a gallium-antimony detector.

14. The method of claim 10, further comprising the step of:

indirectly determining, during an intercrop time period after harvest and prior to planting, a cropland state with readings taken said orbiting satellite; and recommending a plant type to plant on the piece of land based on at least:

said seasonal weather prediction; and readings taken from said orbiting satellite during said intercrop time period.

15. The method of claim 1, further comprising the steps of:

recommending, based on said cropland condition information, a plant type to plant on the cropland.

16. The method of claim 15, further comprising the step of:

comparing results of said optically measuring step to library information on-board said orbiting satellite prior to said step of recommending.

17. The method of claim 1, further comprising the step of:

comparing first nighttime detected emitted radiation in the thermal infrared range of 8,000 to 12,000 nm with second daytime detected emitted radiation in the thermal infrared range of 8,000 to 12,000 nm to yield a measure of ground temperature.

18. A method for managing cropland for a client, comprising the steps of:

optically measuring, each of a set of spatially resolved locations, level zero data with an orbiting satellite, said level zero data comprising:

first reflected cropland radiation, in a visible range of 400 to 1,000 nm;

second reflected cropland radiation in a near-infrared range of 1,000 to 3,000 nm;

third radiation in a range of 3,000 to 5,000 nm; and emitted radiation, in a thermal infrared range of 8,000 to 12,000 nm;

processing, on-board said orbiting satellite, said level zero data comprising a first data storage size, to yield cropland condition information comprising a second data storage size of less than one percent of said first data storage size;

receiving from said orbiting satellite to a ground-based communication system said cropland condition information;

relaying at least a portion of said cropland condition information to the client within twenty-four hours;

determining an immediately previous crop type for a piece of land, said step of determining an immediately previous crop type further comprising at least one of the steps of:

uploading to said orbiting satellite an immediately previous crop type for the piece of land;

previously determining, on-board said orbiting satellite, said immediately previous crop type for the piece of land;

collecting said first reflected cropland radiation with a silicon detector;

collecting said second reflected cropland radiation with an indium-gallium-arsenide detector;

collecting said third radiation with an indium-phosphide detector;

collecting said emitted radiation with a gallium-antimony detector;

inter-crop measuring, after harvest and prior to subsequent crop sprouting, crop soil characteristics of a piece of land with said orbiting satellite, said step of inter-crop measuring further comprising the steps of:

determining a moisture absorbance reading of the piece of land with a water absorbance band measured with said indium-gallium-arsenide detector;

determining a coverage percent of standing biomass with said silicon detector;

indirectly measuring nitrogen through an absorbance measurement of at least one of: nitrate at 1320 nm and ammonia at 3300 $cm^{-1}$; and indirectly measuring nitrogen through a measure of red light with said silicon detector.

19. A method for managing cropland for a client, comprising the steps of:

optically measuring, each of a set of spatially resolved locations, level zero data with an orbiting satellite, said level zero data comprising:

first reflected cropland radiation, in a visible range of 400 to 1,000 nm;

second reflected cropland radiation in a near-infrared range of 1,000 to 3,000 nm;

third radiation in a range of 3,000 to 5,000 nm; and emitted radiation, in a thermal infrared range of 8,000 to 12,000 nm;

processing, on-board said orbiting satellite, said level zero data comprising a first data storage size, to yield cropland condition information comprising a second data storage size of less than one percent of said first data storage size;

receiving from said orbiting satellite to a ground-based communication system said cropland condition information;

relaying at least a portion of said cropland condition information to the client within twenty-four hours;

comparing first nighttime detected emitted radiation in the thermal infrared range of 8,000 to 12,000 nm with second daytime detected emitted radiation in the thermal infrared range of 8,000 to 12,000 nm to yield a measure of ground temperature; and recommending timing of planting based on the measure of ground temperature.

20. The method of claim 19, further comprising the step of:

generating a recommendation of a plant type to plant on-board said orbiting satellite.

* * * * *